(12) United States Patent
Ginn et al.

(10) Patent No.: US 7,819,895 B2
(45) Date of Patent: Oct. 26, 2010

(54) VASCULAR SHEATH WITH BIOABSORBABLE PUNCTURE SITE CLOSURE APPARATUS AND METHODS OF USE

(75) Inventors: Richard S. Ginn, San Jose, CA (US); William N. Aldrich, Napa, CA (US)

(73) Assignee: Integrated Vascular Systems, Inc., Redwood City, CA (US)

( * ) Notice: Subject to any disclaimer, the term of this patent is extended or adjusted under 35 U.S.C. 154(b) by 0 days.

(21) Appl. No.: 11/406,203

(22) Filed: Apr. 18, 2006

(65) Prior Publication Data

US 2006/0195123 A1 Aug. 31, 2006

Related U.S. Application Data

(63) Continuation of application No. 10/264,306, filed on Oct. 3, 2002, which is a continuation of application No. 09/546,998, filed on Apr. 11, 2000, now Pat. No. 6,461,364, which is a continuation-in-part of application No. 09/478,179, filed on Jan. 5, 2000, now Pat. No. 6,197,042.

(51) Int. Cl.
*A61B 17/08* (2006.01)
*A61D 1/00* (2006.01)

(52) U.S. Cl. ...................... 606/219; 606/157

(58) Field of Classification Search .......... 606/139, 606/142, 151, 213, 219, 157, 158, 215, 216, 606/220, 221; 24/536, 537, 515, 503

See application file for complete search history.

(56) References Cited

U.S. PATENT DOCUMENTS

| | | |
|---|---|---|
| 287,046 A | 10/1883 | Norton |
| 438,400 A | 10/1890 | Brennen |
| 1,088,393 A | 2/1914 | Backus |

(Continued)

FOREIGN PATENT DOCUMENTS

| | | |
|---|---|---|
| CA | 2 339 060 | 2/2000 |

(Continued)

OTHER PUBLICATIONS

Database WPI; Section PQ, Week 200120; Derwent Publications Ltd., London GB; AN 2001-203165; XP002199926 & ZA 200 100 528 A (Anthony T), Feb. 28, 2001 abstract.

(Continued)

*Primary Examiner*—Gary Jackson
*Assistant Examiner*—Ryan J Severson
(74) *Attorney, Agent, or Firm*—Workman Nydegger

(57) ABSTRACT

Apparatus and methods are provided for use in sealing a vascular puncture site. The invention comprises an introducer sheath with an integrated closure component. The closure component includes a fastener and an advanceable, deformable clip having a delivery configuration in which opposing sides do not contact one another, and a deployed configuration, in which the fastener causes opposing sides of the deformable clip to close towards one another. The clip is advanced along the sheath until it pierces opposing sides of a vessel wall at a puncture site. The clip is then deformed with the fastener to draw opposing sides of the puncture together, and the sheath is withdrawn to seal the wound. The clip and fastener preferably are bioabsorbable.

20 Claims, 4 Drawing Sheets

U.S. PATENT DOCUMENTS

| | | | |
|---|---|---|---|
| 1,331,401 A | 2/1920 | Summers | |
| 1,426,111 A | 8/1922 | Sacker | |
| 1,516,990 A | 11/1924 | Silverman | |
| 1,596,004 A | 8/1926 | De Bengoa | |
| 1,647,958 A | 11/1927 | Ciarlante | |
| 1,847,347 A | 3/1932 | Maisto | |
| 1,852,098 A | 4/1932 | Anderson | |
| 1,880,569 A | 10/1932 | Weis | |
| 2,075,508 A | 3/1937 | Davidson | |
| 2,087,074 A | 7/1937 | Tucker | |
| 2,254,620 A | 9/1941 | Miller | |
| 2,316,297 A | 4/1943 | Southerland et al. | |
| 2,453,227 A | 11/1948 | James | |
| 2,583,625 A | 1/1952 | Bergan | |
| 2,684,070 A | 7/1954 | Kelsey | |
| 2,910,067 A | 10/1959 | White | |
| 2,944,311 A | 7/1960 | Schneckenberger | |
| 2,951,482 A | 9/1960 | Sullivan | |
| 2,969,887 A | 1/1961 | Darmstadt et al. | |
| 3,014,483 A | 12/1961 | McCarthy | |
| 3,015,403 A | 1/1962 | Fuller | |
| 3,113,379 A | 12/1963 | Frank | |
| 3,120,230 A | 2/1964 | Skold | |
| 3,142,878 A | 8/1964 | Santora | |
| 3,209,754 A | 10/1965 | Brown | |
| 3,482,428 A | 12/1969 | Kapitanov et al. | |
| 3,494,533 A | 2/1970 | Green et al. | |
| 3,513,848 A | 5/1970 | Winston et al. | |
| 3,523,351 A | 8/1970 | Filia | |
| 3,525,340 A | 8/1970 | Gilbert | |
| 3,586,002 A | 6/1971 | Wood | 165/240 |
| 3,604,425 A | 9/1971 | LeRoy | 403/302 |
| 3,618,447 A | 11/1971 | Goins | |
| 3,664,345 A | 5/1972 | Dabbs et al. | |
| 3,677,243 A | 7/1972 | Nerz | 604/161 |
| 3,732,719 A | 5/1973 | Pallotta | |
| 3,750,650 A | 8/1973 | Ruttgers | |
| 3,753,438 A | 8/1973 | Wood et al. | |
| 3,757,629 A | 9/1973 | Schneider | 411/443 |
| 3,805,337 A | 4/1974 | Branstetter | 24/27 |
| 3,828,791 A | 8/1974 | Santos | |
| 3,831,608 A | 8/1974 | Kletschka et al. | |
| 3,856,016 A | 12/1974 | Davis | |
| 3,874,388 A | 4/1975 | King et al. | |
| 3,908,662 A | 9/1975 | Razgulov et al. | |
| 3,931,821 A | 1/1976 | Kletschka et al. | |
| 3,944,114 A | 3/1976 | Coppens | |
| 3,976,079 A | 8/1976 | Samuels et al. | |
| 4,014,492 A | 3/1977 | Rothfuss | |
| 4,064,881 A | 12/1977 | Meredith | |
| 4,162,673 A | 7/1979 | Patel | |
| 4,169,476 A | 10/1979 | Hiltebrandt | |
| 4,192,315 A | 3/1980 | Hilzinger et al. | 606/158 |
| 4,201,215 A | 5/1980 | Crossett et al. | |
| 4,204,541 A | 5/1980 | Kapitanov | |
| 4,207,870 A | 6/1980 | Eldridge | |
| 4,214,587 A | 7/1980 | Sakura, Jr. | |
| 4,215,699 A | 8/1980 | Patel | |
| 4,217,902 A | 8/1980 | March | 606/221 |
| 4,278,091 A | 7/1981 | Borzone | |
| 4,287,489 A | 9/1981 | Pinkham | |
| 4,291,698 A | 9/1981 | Fuchs et al. | |
| 4,317,445 A | 3/1982 | Robinson | |
| 4,318,401 A | 3/1982 | Zimmerman | |
| 4,327,485 A | 5/1982 | Rix | |
| 4,345,606 A | 8/1982 | Littleford | 607/122 |
| 4,368,736 A | 1/1983 | Kaster | |
| 4,387,489 A | 6/1983 | Dudek | |
| 4,396,139 A | 8/1983 | Hall et al. | 227/19 |
| 4,400,879 A | 8/1983 | Hildreth | |
| 4,411,654 A | 10/1983 | Boarini et al. | 604/165.4 |
| 4,412,832 A | 11/1983 | Kling et al. | 604/164.05 |
| 4,428,376 A | 1/1984 | Mericle | |
| 4,440,170 A | 4/1984 | Golden et al. | |
| 4,480,356 A | 11/1984 | Martin | |
| 4,485,816 A | 12/1984 | Krumme | 606/219 |
| RE31,855 E | 3/1985 | Osborne | 604/161 |
| 4,505,273 A | 3/1985 | Braun et al. | |
| 4,505,274 A | 3/1985 | Speelman | 606/221 |
| 4,523,695 A | 6/1985 | Braun et al. | |
| 4,525,157 A | 6/1985 | Valaincourt | |
| 4,526,174 A | 7/1985 | Froehlich | |
| 4,577,635 A | 3/1986 | Meredith | |
| 4,586,503 A | 5/1986 | Kirsch et al. | 606/155 |
| 4,607,638 A | 8/1986 | Crainich | |
| 4,610,251 A | 9/1986 | Kumar | |
| 4,610,252 A | 9/1986 | Catalano | |
| 4,635,634 A | 1/1987 | Santos | |
| 4,644,956 A | 2/1987 | Morgenstern | |
| 4,665,906 A | 5/1987 | Jervis | |
| 4,667,675 A | 5/1987 | Davis | |
| 4,683,895 A | 8/1987 | Pohndorf | |
| 4,687,469 A | 8/1987 | Osypka | 604/161 |
| 4,719,917 A | 1/1988 | Barrows et al. | |
| 4,724,840 A | 2/1988 | McVay et al. | |
| 4,738,658 A | 4/1988 | Magro et al. | |
| 4,744,364 A | 5/1988 | Kensey | |
| 4,747,407 A | 5/1988 | Liu et al. | |
| 4,750,492 A | 6/1988 | Jacobs | |
| 4,759,364 A | 7/1988 | Boebel | |
| 4,771,782 A | 9/1988 | Millar | |
| 4,772,266 A | 9/1988 | Groshong | 604/164.05 |
| 4,773,421 A | 9/1988 | Davis | |
| 4,777,950 A | 10/1988 | Kees, Jr. | 606/158 |
| 4,789,090 A | 12/1988 | Blake, III | |
| 4,813,586 A | 3/1989 | Seifert | |
| 4,823,794 A | 4/1989 | Pierce | |
| 4,832,688 A | 5/1989 | Sagae et al. | |
| 4,836,204 A | 6/1989 | Landymore et al. | |
| 4,852,568 A | 8/1989 | Kensey | |
| 4,860,746 A | 8/1989 | Yoon | 128/830 |
| 4,865,026 A | 9/1989 | Barrett | 606/214 |
| 4,866,818 A | 9/1989 | Thompson | |
| 4,874,122 A | 10/1989 | Froelich et al. | |
| 4,878,915 A | 11/1989 | Brantigan | |
| 4,887,601 A * | 12/1989 | Richards | 606/219 |
| 4,917,087 A | 4/1990 | Walsh et al. | 606/153 |
| 4,917,089 A | 4/1990 | Sideris | |
| 4,929,240 A | 5/1990 | Kirsch et al. | |
| 4,934,364 A | 6/1990 | Green | |
| 4,950,258 A | 8/1990 | Kawai et al. | 604/530 |
| 4,957,499 A | 9/1990 | Lipatov et al. | |
| 4,961,729 A | 10/1990 | Vaillancourt | |
| 4,997,436 A | 3/1991 | Oberlander | |
| 4,997,439 A | 3/1991 | Chen | |
| 5,002,562 A | 3/1991 | Oberlander | |
| 5,007,921 A | 4/1991 | Brown | 606/221 |
| 5,009,663 A | 4/1991 | Broomé | |
| 5,015,247 A | 5/1991 | Michelson | |
| 5,021,059 A | 6/1991 | Kensey et al. | |
| 5,026,390 A | 6/1991 | Brown | 606/221 |
| 5,032,127 A | 7/1991 | Frazee et al. | |
| 5,047,047 A | 9/1991 | Yoon | |
| 5,053,008 A | 10/1991 | Bajaj | 604/104 |
| 5,059,201 A | 10/1991 | Asnis | |
| 5,061,274 A | 10/1991 | Kensey | 606/213 |
| 5,071,430 A | 12/1991 | de Salis et al. | |
| 5,078,731 A | 1/1992 | Hayhurst | |
| 5,092,941 A | 3/1992 | Miura | |
| 5,100,418 A | 3/1992 | Yoon et al. | 606/139 |
| 5,108,420 A | 4/1992 | Marks | 606/213 |
| 5,108,421 A | 4/1992 | Fowler | |
| 5,114,032 A | 5/1992 | Laidlaw | |
| 5,114,065 A | 5/1992 | Storace | |

| Patent No. | Date | Inventor | Class |
|---|---|---|---|
| 5,116,349 A | 5/1992 | Aranyi | |
| 5,122,122 A | 6/1992 | Allgood | |
| 5,122,156 A | 6/1992 | Granger et al. | |
| 5,131,379 A | 7/1992 | Sewell, Jr. | |
| 5,147,381 A | 9/1992 | Heimerl et al. | |
| 5,156,609 A * | 10/1992 | Nakao et al. | 606/142 |
| 5,158,566 A | 10/1992 | Pianetti | |
| 5,160,339 A | 11/1992 | Chen et al. | |
| 5,167,634 A | 12/1992 | Corrigan, Jr. et al. | |
| 5,167,643 A | 12/1992 | Lynn | 604/263 |
| 5,171,249 A | 12/1992 | Stefanchik et al. | 606/142 |
| 5,171,250 A | 12/1992 | Yoon | |
| 5,171,251 A | 12/1992 | Bregen et al. | |
| 5,176,648 A | 1/1993 | Holmes et al. | 604/180 |
| 5,176,682 A | 1/1993 | Chow | |
| 5,192,288 A | 3/1993 | Thompson et al. | |
| 5,192,300 A | 3/1993 | Fowler | |
| 5,192,301 A | 3/1993 | Kamiya et al. | |
| 5,192,302 A | 3/1993 | Kensey et al. | 606/213 |
| 5,192,602 A | 3/1993 | Spencer et al. | |
| 5,203,787 A | 4/1993 | Noblitt et al. | |
| 5,209,756 A | 5/1993 | Seedhom et al. | |
| 5,217,024 A | 6/1993 | Dorsey et al. | |
| 5,219,359 A | 6/1993 | McQuilkin et al. | |
| 5,222,974 A | 6/1993 | Kensey et al. | 606/213 |
| 5,226,908 A | 7/1993 | Yoon | |
| 5,234,449 A | 8/1993 | Bruker et al. | |
| 5,236,435 A | 8/1993 | Sewell, Jr. | |
| 5,236,445 A | 8/1993 | Hayhurst et al. | |
| 5,242,457 A | 9/1993 | Akopov et al. | |
| 5,242,459 A | 9/1993 | Buelna | |
| 5,246,156 A | 9/1993 | Rothfuss et al. | |
| 5,246,443 A | 9/1993 | Mai | |
| 5,250,058 A * | 10/1993 | Miller et al. | 606/154 |
| 5,258,015 A | 11/1993 | Li et al. | |
| 5,269,792 A | 12/1993 | Kovac et al. | |
| 5,275,616 A | 1/1994 | Fowler | 606/213 |
| 5,282,808 A | 2/1994 | Kovac et al. | |
| 5,282,832 A | 2/1994 | Toso et al. | |
| 5,290,243 A | 3/1994 | Chodorow et al. | |
| 5,290,310 A | 3/1994 | Makower et al. | |
| 5,292,309 A | 3/1994 | Van Tassel et al. | |
| 5,292,332 A | 3/1994 | Lee | |
| 5,304,184 A | 4/1994 | Hathaway et al. | 606/144 |
| 5,304,204 A | 4/1994 | Bregen | |
| 5,306,254 A | 4/1994 | Nash et al. | |
| 5,306,280 A | 4/1994 | Bregen et al. | |
| 5,318,542 A | 6/1994 | Hirsch et al. | 606/161 |
| 5,320,639 A | 6/1994 | Rudnick | |
| 5,330,442 A | 7/1994 | Green et al. | |
| 5,334,216 A | 8/1994 | Vidal et al. | |
| 5,334,217 A | 8/1994 | Das | 606/213 |
| 5,335,680 A | 8/1994 | Moore | |
| 5,340,360 A | 8/1994 | Stefanchik | |
| 5,350,399 A | 9/1994 | Erlebacher et al. | |
| 5,352,229 A | 10/1994 | Goble et al. | |
| 5,364,406 A | 11/1994 | Sewell, Jr. | |
| 5,364,408 A | 11/1994 | Gordon | |
| 5,366,458 A | 11/1994 | Korthoff et al. | 606/151 |
| 5,366,479 A | 11/1994 | McGarry et al. | |
| 5,376,101 A | 12/1994 | Green et al. | |
| 5,383,896 A | 1/1995 | Gershony et al. | |
| 5,383,905 A | 1/1995 | Golds et al. | |
| RE34,866 E | 2/1995 | Kensey et al. | |
| 5,243,857 A | 2/1995 | Velez | |
| 5,391,173 A | 2/1995 | Wilk | |
| 5,392,978 A | 2/1995 | Velez et al. | |
| 5,395,030 A | 3/1995 | Kuramoto et al. | |
| 5,409,499 A | 4/1995 | Yi | |
| 5,411,520 A | 5/1995 | Nash et al. | |
| 5,413,571 A | 5/1995 | Katsaros et al. | |
| 5,413,584 A | 5/1995 | Schulze | |
| 5,416,584 A | 5/1995 | Kay | |
| 5,417,699 A | 5/1995 | Klein et al. | |
| 5,419,777 A | 5/1995 | Hofling | |
| 5,423,857 A * | 6/1995 | Rosenman et al. | 606/219 |
| 5,425,489 A | 6/1995 | Shichman et al. | |
| 5,431,639 A | 7/1995 | Shaw | |
| 5,431,667 A | 7/1995 | Thompson et al. | |
| 5,437,631 A | 8/1995 | Janzen | |
| 5,443,477 A | 8/1995 | Marin et al. | |
| 5,443,481 A | 8/1995 | Lee | |
| 5,449,359 A | 9/1995 | Groiso | |
| 5,456,400 A | 10/1995 | Shichman et al. | |
| 5,462,558 A | 10/1995 | Kolesa et al. | |
| 5,462,561 A | 10/1995 | Voda | |
| 5,470,010 A | 11/1995 | Rothfuss et al. | |
| 5,474,557 A | 12/1995 | Mai | |
| 5,474,572 A | 12/1995 | Hayhurst | |
| 5,478,352 A | 12/1995 | Fowler | |
| 5,478,353 A | 12/1995 | Yoon | 606/213 |
| 5,478,354 A * | 12/1995 | Tovey et al. | 606/219 |
| 5,486,195 A | 1/1996 | Myers et al. | |
| 5,497,933 A | 3/1996 | DeFonzo et al. | |
| 5,501,698 A | 3/1996 | Roth et al. | |
| 5,507,744 A | 4/1996 | Tay et al. | |
| 5,507,755 A | 4/1996 | Gresl et al. | 606/139 |
| 5,514,159 A | 5/1996 | Matula et al. | |
| 5,521,184 A | 5/1996 | Zimmermann | |
| 5,522,840 A | 6/1996 | Krajicek | |
| 5,527,322 A | 6/1996 | Klein et al. | 606/144 |
| 5,536,251 A | 7/1996 | Evard et al. | |
| 5,540,712 A | 7/1996 | Kleshinski et al. | |
| 5,540,716 A | 7/1996 | Hlavacek | |
| 5,543,520 A | 8/1996 | Zimmermann | |
| 5,544,802 A | 8/1996 | Crainich | |
| 5,547,474 A | 8/1996 | Kloeckl et al. | |
| 5,560,532 A | 10/1996 | DeFonzo et al. | |
| 5,575,771 A | 11/1996 | Walinsky | |
| 5,584,879 A | 12/1996 | Reimold et al. | |
| 5,591,205 A | 1/1997 | Fowler | |
| 5,593,412 A | 1/1997 | Martinez | |
| 5,593,422 A | 1/1997 | Muijs Van der Moer et al. | |
| 5,593,425 A | 1/1997 | Bonutti et al. | |
| 5,601,602 A | 2/1997 | Fowler | |
| 5,611,986 A | 3/1997 | Datta et al. | |
| 5,618,291 A | 4/1997 | Thompson et al. | |
| 5,618,306 A | 4/1997 | Roth et al. | |
| 5,620,452 A | 4/1997 | Yoon | |
| 5,620,461 A | 4/1997 | Muijs et al. | |
| 5,630,824 A | 5/1997 | Hart | |
| 5,643,318 A | 7/1997 | Tsukernik et al. | |
| 5,645,553 A | 7/1997 | Kolesa et al. | |
| 5,645,565 A | 7/1997 | Rudd et al. | |
| 5,645,566 A | 7/1997 | Brenneman et al. | |
| 5,645,567 A | 7/1997 | Crainich | |
| D383,539 S | 9/1997 | Croley | |
| 5,669,917 A | 9/1997 | Sauer et al. | |
| 5,674,231 A | 10/1997 | Green et al. | 606/142 |
| 5,676,689 A | 10/1997 | Kensey et al. | |
| 5,676,974 A | 10/1997 | Valdes et al. | |
| 5,681,334 A | 10/1997 | Evans et al. | |
| 5,681,351 A | 10/1997 | Jamiolkowski et al. | |
| 5,683,405 A | 11/1997 | Yacoubian et al. | 606/158 |
| 5,690,674 A | 11/1997 | Diaz | |
| 5,695,504 A * | 12/1997 | Gifford et al. | 606/153 |
| 5,695,505 A | 12/1997 | Yoon | 606/157 |
| 5,695,524 A | 12/1997 | Kelley et al. | |
| 5,700,273 A | 12/1997 | Buelna et al. | |
| 5,709,708 A | 1/1998 | Thal | |
| 5,716,375 A | 2/1998 | Fowler | |
| 5,720,755 A | 2/1998 | Dakov | |
| 5,720,765 A | 2/1998 | Thal | |
| 5,725,498 A | 3/1998 | Janzen et al. | |
| 5,725,552 A | 3/1998 | Kotula et al. | |
| 5,725,554 A | 3/1998 | Simon et al. | |

| | | |
|---|---|---|
| 5,725,556 A | 3/1998 | Moser et al. |
| 5,728,109 A | 3/1998 | Schulze et al. |
| 5,728,110 A | 3/1998 | Vidal et al. |
| 5,728,114 A | 3/1998 | Evans et al. .................. 606/148 |
| 5,728,122 A | 3/1998 | Leschinsky et al. |
| 5,728,132 A | 3/1998 | Van Tassel et al. |
| 5,732,872 A | 3/1998 | Bolduc et al. |
| 5,735,873 A | 4/1998 | MacLean |
| 5,735,875 A | 4/1998 | Bonutti et al. |
| 5,735,877 A | 4/1998 | Pagedas |
| 5,749,898 A | 5/1998 | Schulze et al. |
| 5,752,966 A | 5/1998 | Chang |
| 5,755,726 A | 5/1998 | Pratt et al. |
| 5,755,778 A | 5/1998 | Kleshinski |
| 5,766,246 A | 6/1998 | Mulhauser et al. |
| 5,769,862 A | 6/1998 | Kammerer et al. |
| 5,769,870 A | 6/1998 | Salahieh et al. |
| 5,776,150 A | 7/1998 | Nolan et al. |
| 5,779,707 A | 7/1998 | Bertholet et al. |
| 5,782,844 A | 7/1998 | Yoon et al. .................. 606/139 |
| 5,782,860 A | 7/1998 | Epstein et al. .............. 606/213 |
| 5,782,861 A | 7/1998 | Cragg et al. ................ 606/216 |
| 5,782,864 A | 7/1998 | Lizardi |
| 5,795,958 A | 8/1998 | Rao et al. |
| 5,797,931 A | 8/1998 | Bito et al. |
| 5,797,933 A | 8/1998 | Snow et al. |
| 5,797,958 A | 8/1998 | Yoon |
| 5,810,776 A | 9/1998 | Bacich et al. |
| 5,810,846 A | 9/1998 | Virnich et al. .............. 606/142 |
| 5,810,851 A | 9/1998 | Yoon ........................... 606/148 |
| 5,810,877 A | 9/1998 | Roth et al. |
| 5,814,069 A | 9/1998 | Schulze et al. |
| 5,817,113 A | 10/1998 | Gifford et al. .............. 606/153 |
| 5,820,631 A | 10/1998 | Nobles ........................ 606/213 |
| 5,827,298 A | 10/1998 | Hart et al. |
| 5,830,125 A | 11/1998 | Scribner et al. ............. 606/139 |
| 5,833,698 A | 11/1998 | Hinchliffe et al. |
| 5,843,167 A | 12/1998 | Dwyer et al. |
| 5,846,254 A | 12/1998 | Schulze et al. |
| 5,853,421 A | 12/1998 | Leschinsky et al. |
| 5,853,422 A | 12/1998 | Huebsch et al. |
| 5,855,312 A | 1/1999 | Toledano |
| 5,858,082 A | 1/1999 | Cruz et al. |
| 5,860,991 A | 1/1999 | Klein et al. |
| 5,861,005 A | 1/1999 | Kontos |
| 5,868,755 A | 2/1999 | Kanner et al. |
| 5,871,474 A | 2/1999 | Hermann et al. |
| 5,871,490 A | 2/1999 | Schulze et al. |
| 5,871,501 A | 2/1999 | Leschinsky et al. |
| 5,871,525 A | 2/1999 | Edwards et al. |
| 5,879,366 A | 3/1999 | Shaw et al. ................. 606/213 |
| 5,893,592 A | 4/1999 | Schulze et al. |
| 5,897,487 A | 4/1999 | Ouchi |
| 5,902,310 A | 5/1999 | Foerster et al. |
| 5,904,697 A | 5/1999 | Gifford, III et al. |
| 5,907,893 A | 6/1999 | Zadno-Azizi et al. |
| 5,910,155 A | 6/1999 | Ratcliff et al. .............. 606/213 |
| 5,919,208 A | 7/1999 | Valenti |
| 5,922,009 A | 7/1999 | Epstein et al. .............. 606/213 |
| 5,935,147 A | 8/1999 | Kensey et al. ............... 606/213 |
| 5,938,667 A | 8/1999 | Peyser et al. |
| 5,941,890 A | 8/1999 | Voegele et al. |
| 5,947,999 A * | 9/1999 | Groiso ........................ 606/219 |
| 5,951,518 A | 9/1999 | Licata et al. ................. 604/161 |
| 5,951,576 A | 9/1999 | Wakabayashi |
| 5,951,589 A | 9/1999 | Epstein et al. .............. 606/213 |
| 5,964,782 A | 10/1999 | LaFontaine et al. ......... 606/213 |
| 5,976,159 A | 11/1999 | Bolduc et al. |
| 5,984,934 A | 11/1999 | Ashby et al. ................ 606/151 |
| 5,984,949 A | 11/1999 | Levin |
| 5,993,468 A | 11/1999 | Rygaard |
| 5,993,476 A * | 11/1999 | Groiso ........................ 606/219 |
| 6,001,110 A | 12/1999 | Adams |
| 6,004,341 A | 12/1999 | Zhu et al. |
| 6,007,563 A | 12/1999 | Nash et al. .................. 606/213 |
| 6,022,372 A | 2/2000 | Kontos |
| 6,024,750 A | 2/2000 | Mastri |
| 6,024,758 A | 2/2000 | Thal |
| 6,030,364 A | 2/2000 | Durgin et al. |
| 6,030,413 A | 2/2000 | Lazarus |
| 6,033,427 A | 3/2000 | Lee |
| 6,036,703 A | 3/2000 | Evans et al. |
| 6,036,720 A | 3/2000 | Abrams et al. .............. 606/213 |
| 6,045,570 A | 4/2000 | Epstein et al. .............. 606/214 |
| 6,048,358 A | 4/2000 | Barak |
| 6,056,768 A | 5/2000 | Cates et al. |
| 6,056,769 A | 5/2000 | Epstein et al. .............. 606/213 |
| 6,056,770 A | 5/2000 | Epstein et al. |
| 6,059,800 A | 5/2000 | Hart et al. |
| 6,063,085 A | 5/2000 | Tay et al. ..................... 606/50 |
| 6,063,114 A | 5/2000 | Nash et al. |
| 6,066,160 A | 5/2000 | Colvin et al. |
| 6,071,300 A | 6/2000 | Brenneman et al. |
| 6,074,409 A | 6/2000 | Goldfarb |
| 6,077,281 A | 6/2000 | Das ............................. 606/151 |
| 6,077,291 A | 6/2000 | Das ............................. 606/213 |
| 6,080,182 A | 6/2000 | Shaw ........................... 606/213 |
| 6,080,183 A | 6/2000 | Tsugita et al. ............... 606/213 |
| 6,086,608 A | 7/2000 | Ek et al. |
| 6,090,130 A | 7/2000 | Nash et al. |
| 6,092,561 A | 7/2000 | Schmid |
| 6,099,553 A | 8/2000 | Hart et al. |
| 6,102,271 A | 8/2000 | Longo et al. |
| 6,106,545 A | 8/2000 | Egan |
| 6,110,184 A | 8/2000 | Weadock ..................... 606/144 |
| 6,113,612 A | 9/2000 | Swanson et al. |
| 6,117,125 A | 9/2000 | Rothbarth et al. |
| 6,117,148 A | 9/2000 | Ravo |
| 6,120,524 A | 9/2000 | Taheri ......................... 606/213 |
| 6,126,677 A | 10/2000 | Ganaja et al. |
| 6,136,010 A | 10/2000 | Modesitt et al. |
| 6,143,017 A | 11/2000 | Thal |
| 6,149,660 A | 11/2000 | Laufer et al. |
| 6,149,667 A * | 11/2000 | Hovland et al. .............. 606/219 |
| 6,152,144 A | 11/2000 | Lesh et al. |
| 6,152,934 A | 11/2000 | Harper et al. |
| 6,152,937 A | 11/2000 | Peterson et al. |
| 6,159,234 A | 12/2000 | Bonutti et al. |
| 6,165,204 A | 12/2000 | Levinson et al. |
| 6,174,324 B1 | 1/2001 | Egan et al. |
| 6,193,734 B1 | 2/2001 | Bolduc et al. |
| 6,197,042 B1 | 3/2001 | Ginn et al. .................. 606/213 |
| 6,200,329 B1 | 3/2001 | Fung et al. |
| 6,203,565 B1 | 3/2001 | Bonutti et al. |
| 6,206,913 B1 | 3/2001 | Yencho et al. |
| 6,220,248 B1 | 4/2001 | Voegele et al. |
| 6,221,102 B1 | 4/2001 | Baker et al. |
| 6,231,592 B1 | 5/2001 | Bonutti et al. |
| 6,254,615 B1 | 7/2001 | Bolduc et al. |
| 6,254,642 B1 | 7/2001 | Taylor |
| 6,277,140 B1 | 8/2001 | Ginn et al. .................. 606/213 |
| 6,280,460 B1 | 8/2001 | Bolduc et al. |
| 6,287,322 B1 | 9/2001 | Zhu et al. |
| 6,305,891 B1 | 10/2001 | Burlingame |
| 6,322,580 B1 | 11/2001 | Kanner |
| 6,334,865 B1 | 1/2002 | Redmond et al. ............ 606/213 |
| 6,348,064 B1 | 2/2002 | Kanner ........................ 606/219 |
| 6,780,197 B2 | 2/2002 | Carley et al. |
| D457,958 S | 5/2002 | Dycus |
| 6,383,208 B1 | 5/2002 | Sancoff et al. |
| 6,391,048 B1 | 5/2002 | Ginn et al. .................. 606/213 |
| 6,398,752 B1 | 6/2002 | Sweezer et al. |
| 6,402,765 B1 | 6/2002 | Monassevitch et al. |
| 6,409,739 B1 | 6/2002 | Nobles et al. ............... 606/148 |
| 6,419,669 B1 | 7/2002 | Frazier et al. |
| 6,423,054 B1 | 7/2002 | Ouchi |

| | | | | | |
|---|---|---|---|---|---|
| 6,428,548 B1 | 8/2002 | Durgin et al. | 2001/0047180 A1 | 11/2001 | Grudem et al. |
| 6,443,158 B1 | 9/2002 | Lafontaine et al. | 2002/0026208 A1 | 2/2002 | Belef |
| 6,447,540 B1 | 9/2002 | Fontaine et al. | 2002/0026215 A1 | 2/2002 | Redmond et al. ........... 606/213 |
| 6,450,391 B1 | 9/2002 | Kayan et al. | 2002/0042622 A1 | 4/2002 | Vargas et al. |
| 6,458,130 B1 | 10/2002 | Frazier et al. | 2002/0049472 A1 | 4/2002 | Coleman et al. |
| 6,461,364 B1 | 10/2002 | Ginn et al. | 2002/0058960 A1 | 5/2002 | Hudson et al. |
| 6,488,692 B1 | 12/2002 | Spence et al. | 2002/0072768 A1 | 6/2002 | Ginn ......................... 606/213 |
| 6,500,115 B2 | 12/2002 | Krattiger et al. | 2002/0077657 A1 | 6/2002 | Ginn et al. .................. 606/213 |
| 6,506,210 B1 | 1/2003 | Kanner | 2002/0082641 A1 | 6/2002 | Ginn et al. |
| 6,517,569 B2 | 2/2003 | Mikus et al. | 2002/0107542 A1 | 8/2002 | Kanner et al. |
| 6,533,762 B2 | 3/2003 | Kanner et al. | 2002/0133193 A1 | 9/2002 | Ginn et al. |
| 6,537,288 B2 | 3/2003 | Vargas et al. | 2002/0151921 A1 | 10/2002 | Kanner et al. |
| 6,547,806 B1 | 4/2003 | Ding ......................... 606/213 | 2002/0188318 A1 | 12/2002 | Carley et al. ................. 606/213 |
| 6,569,173 B1 | 5/2003 | Blatter et al. | 2002/0193808 A1 | 12/2002 | Belef et al. .................. 606/139 |
| 6,582,452 B2 | 6/2003 | Coleman et al. ............ 606/213 | 2003/0004543 A1 | 1/2003 | Gleeson et al. |
| 6,582,482 B2 | 6/2003 | Gillman et al. | 2003/0009180 A1 | 1/2003 | Hinchliffe et al. ........... 606/144 |
| 6,599,303 B1 | 7/2003 | Peterson et al. | 2003/0009196 A1 | 1/2003 | Peterson |
| 6,602,263 B1 | 8/2003 | Swanson et al. | 2003/0032981 A1 | 2/2003 | Kanner et al. |
| 6,613,059 B2 | 9/2003 | Schaller et al. | 2003/0065358 A1 | 4/2003 | Frecker et al. |
| 6,616,686 B2 | 9/2003 | Coleman et al. | 2003/0078598 A1 | 4/2003 | Ginn et al. .................. 606/142 |
| 6,623,510 B2 | 9/2003 | Carley et al. | 2003/0083679 A1 | 5/2003 | Grudem et al. |
| 6,626,918 B1 | 9/2003 | Ginn et al. | 2003/0093096 A1 | 5/2003 | McGuckin et al. .......... 606/157 |
| 6,632,238 B2 | 10/2003 | Ginn et al. .................. 606/213 | 2003/0097140 A1 | 5/2003 | Kanner |
| 6,634,537 B2 | 10/2003 | Chen | 2003/0109890 A1 | 6/2003 | Kanner et al. |
| 6,645,205 B2 | 11/2003 | Ginn | 2003/0125766 A1 | 7/2003 | Ding ......................... 606/213 |
| 6,652,538 B2 | 11/2003 | Kayan et al. | 2003/0158577 A1 | 8/2003 | Ginn et al. .................. 606/213 |
| 6,652,556 B1 | 11/2003 | VanTassel et al. | 2003/0158578 A1 | 8/2003 | Pantages et al. ............. 606/213 |
| 6,669,714 B2 | 12/2003 | Coleman et al. | 2003/0195504 A1 | 10/2003 | Tallarida et al. |
| 6,676,671 B2 | 1/2004 | Robertson et al. | 2003/0195561 A1 | 10/2003 | Carley et al. |
| 6,679,904 B2 | 1/2004 | Gleeson et al. | 2004/0009289 A1 | 1/2004 | Carley et al. |
| 6,689,147 B1 | 2/2004 | Koster, Jr. | 2004/0010285 A1 | 1/2004 | Carley et al. |
| 6,695,867 B2 | 2/2004 | Ginn et al. .................. 606/213 | 2004/0039414 A1 | 2/2004 | Carley et al. |
| 6,699,256 B1 | 3/2004 | Logan et al. | 2004/0073236 A1 | 4/2004 | Carley et al. |
| 6,702,826 B2 | 3/2004 | Liddicoat et al. | 2004/0073255 A1 | 4/2004 | Ginn et al. |
| 6,712,836 B1 | 3/2004 | Berg et al. | 2004/0082906 A1 | 4/2004 | Tallarida et al. |
| 6,719,777 B2 | 4/2004 | Ginn et al. | 2004/0087985 A1 | 5/2004 | Loshakove et al. |
| 6,726,704 B1 | 4/2004 | Loshakove et al. | 2004/0092964 A1 | 5/2004 | Modesitt et al. |
| 6,743,243 B1 | 6/2004 | Roy et al. | 2004/0092968 A1 | 5/2004 | Caro et al. |
| 6,749,621 B2 | 6/2004 | Pantages et al. | 2004/0097978 A1 | 5/2004 | Modesitt et al. |
| 6,749,622 B2 | 6/2004 | McGuckin et al. | 2004/0153122 A1 | 8/2004 | Palermo |
| 6,755,842 B2 | 6/2004 | Kanner et al. | 2004/0153123 A1 | 8/2004 | Palermo et al. |
| 6,767,356 B2 | 7/2004 | Kanner et al. | 2004/0158127 A1 | 8/2004 | Okada |
| 6,846,319 B2 | 1/2005 | Ginn et al. | 2004/0167570 A1 | 8/2004 | Pantages |
| 6,896,687 B2 | 5/2005 | Dakov | 2004/0254591 A1 | 12/2004 | Kanner et al. |
| 6,926,723 B1 | 8/2005 | Mulhauser et al. | 2004/0267312 A1 | 12/2004 | Kanner et al. |
| 6,926,731 B2 | 8/2005 | Coleman et al. ............ 606/213 | 2005/0059982 A1 | 3/2005 | Zung et al. |
| 6,942,674 B2 | 9/2005 | Belef et al. | 2005/0090859 A1 | 4/2005 | Ravlkumar |
| 6,942,691 B1 | 9/2005 | Chuter | 2005/0119695 A1 | 6/2005 | Carley et al. |
| 6,964,668 B2 | 11/2005 | Modesitt et al. | 2005/0165357 A1 | 7/2005 | McGuckin et al. |
| 6,989,003 B2 | 1/2006 | Wing et al. | 2005/0216057 A1 | 9/2005 | Coleman et al. |
| 6,989,016 B2 | 1/2006 | Tallarida et al. | 2005/0234508 A1 | 10/2005 | Cummins et al. |
| 7,001,398 B2 | 2/2006 | Carley et al. | 2005/0267530 A1 | 12/2005 | Cummins et al. |
| 7,001,400 B1 | 2/2006 | Modesitt et al. | 2005/0273136 A1 | 12/2005 | Belef et al. |
| 7,008,435 B2 | 3/2006 | Cummins | 2005/0274768 A1 | 12/2005 | Cummins et al. |
| 7,008,439 B1 | 3/2006 | Janzen et al. | 2005/0283188 A1 | 12/2005 | Loshakove et al. |
| 7,033,379 B2 | 4/2006 | Peterson | 2006/0020270 A1 | 1/2006 | Jabba et al. |
| 7,060,084 B1 | 6/2006 | Loshakove et al. | 2006/0135989 A1 | 6/2006 | Carley et al. |
| 7,063,711 B1 | 6/2006 | Loshakove et al. | 2006/0144479 A1 | 7/2006 | Carley et al. |
| 7,108,709 B2 | 9/2006 | Cummins | 2006/0167484 A1 | 7/2006 | Carley et al. |
| 7,108,710 B2 | 9/2006 | Anderson | 2006/0190014 A1 | 8/2006 | Ginn et al. |
| 7,111,768 B2 | 9/2006 | Cummins et al. | 2006/0190037 A1 | 8/2006 | Carley et al. |
| 7,144,411 B2 | 12/2006 | Ginn et al. | 2006/0190038 A1 | 8/2006 | Carley et al. |
| 7,163,551 B2 | 1/2007 | Anthony et al. | 2006/0195124 A1 | 8/2006 | Ginn et al. |
| 7,169,158 B2 | 1/2007 | Sniffin et al. | 2006/0265012 A1 | 11/2006 | Anderson |
| 7,169,164 B2 | 1/2007 | Borillo et al. | 2006/0287674 A1 | 12/2006 | Ginn et al. |
| 7,211,101 B2 | 5/2007 | Carley et al. | 2007/0010853 A1 | 1/2007 | Ginn et al. |
| D566,272 S | 4/2008 | Walburg et al. | 2007/0010854 A1 | 1/2007 | Cummins et al. |
| 7,396,359 B1 | 7/2008 | Derowe et al. | 2007/0021778 A1 | 1/2007 | Carly |
| 7,533,790 B1 | 5/2009 | Knodel et al. | 2007/0250080 A1 | 10/2007 | Jones et al. |
| 7,597,706 B2 | 10/2009 | Kanner et al. | 2008/0004636 A1 | 1/2008 | Walberg |
| D611,144 S | 3/2010 | Reynolds | 2008/0065152 A1 | 3/2008 | Carley |
| 2001/0007077 A1 | 7/2001 | Ginn et al. | 2008/0086075 A1 | 4/2008 | Isik et al. |
| 2001/0031972 A1 | 10/2001 | Robertson et al. | 2008/0221616 A1 | 9/2008 | Ginn et al. |

| | | | |
|---|---|---|---|
| 2008/0312686 A1 | 12/2008 | Ellingwood | |
| 2008/0319475 A1 | 12/2008 | Clark | |
| 2009/0157101 A1 | 6/2009 | Reyes et al. | |
| 2009/0157102 A1 | 6/2009 | Reynolds et al. | |
| 2009/0157103 A1 | 6/2009 | Walberg et al. | |

FOREIGN PATENT DOCUMENTS

| | | |
|---|---|---|
| DE | 197 11 288 | 1/1998 |
| DE | 297 23 736 U 1 | 4/1999 |
| DE | 19859952 | 2/2000 |
| EP | 0 386 361 | 9/1990 |
| EP | 0 534 696 | 3/1993 |
| EP | 0 756 851 | 2/1997 |
| EP | 0 774 237 | 5/1997 |
| EP | 0 858 776 | 8/1998 |
| EP | 0 941 697 | 9/1999 |
| FR | 2 443 238 | 7/1980 |
| FR | 2 715 290 | 7/1995 |
| FR | 2 722 975 | 2/1996 |
| GB | 1 358 466 | 7/1974 |
| GB | 2 075 144 | 11/1981 |
| IE | S 2000/0722 | 10/2001 |
| IE | S 2000/0724 | 10/2001 |
| IE | S 2001/0547 | 7/2002 |
| IE | S 2001/0815 | 7/2002 |
| IE | S 2001/0748 | 8/2002 |
| IE | S 2001/0749 | 8/2002 |
| IE | S 2002/0452 | 12/2002 |
| IE | S 2002/0664 | 2/2003 |
| IE | S 2002/0665 | 2/2003 |
| IE | S 2002/0451 | 7/2003 |
| IE | S 2002/0552 | 7/2003 |
| IE | S 2003/0424 | 12/2003 |
| IE | S 2003/0490 | 1/2004 |
| IE | S 2004/0368 | 11/2005 |
| IE | S 2005/0342 | 11/2005 |
| JP | 58-181006 | 12/1983 |
| JP | 12 74750 | 11/1989 |
| JP | 11500642 | 8/1997 |
| NL | 9302140 | 7/1995 |
| PL | 171425 | 4/1997 |
| RU | 2086192 | 8/1997 |
| SU | 197801 | 6/1967 |
| SU | 495067 | 12/1975 |
| SU | 912155 | 3/1982 |
| SU | 1243708 | 7/1986 |
| SU | 1324650 | 7/1987 |
| SU | 1405828 | 6/1988 |
| SU | 1456109 | 2/1989 |
| SU | 1560133 | 4/1990 |
| WO | WO 95/21573 | 8/1995 |
| WO | WO 96/24291 | 8/1996 |
| WO | WO 97/07741 | 3/1997 |
| WO | WO 97/20505 | 6/1997 |
| WO | WO 97/27897 | 8/1997 |
| WO | WO 97/28745 | 8/1997 |
| WO | WO 98/06346 | 2/1998 |
| WO | WO 98/06448 | 2/1998 |
| WO | WO 98/16161 | 4/1998 |
| WO | WO 98/17179 | 4/1998 |
| WO | WO 98/18389 | 5/1998 |
| WO | WO 98/24374 | 6/1998 |
| WO | WO 98/25508 | 6/1998 |
| WO | WO 98/58591 | 12/1998 |
| WO | WO 99/21491 | 5/1999 |
| WO | WO 99/60941 | 12/1999 |
| WO | WO 99/62408 | 12/1999 |
| WO | WO 99/62415 | 12/1999 |
| WO | WO 00/06029 | 2/2000 |
| WO | WO 00/07505 | 2/2000 |
| WO | WO 00/07640 | 2/2000 |
| WO | WO 00/27311 | 5/2000 |
| WO | WO 00/27313 | 5/2000 |
| WO | WO 00/56223 | 9/2000 |
| WO | WO 00/56227 | 9/2000 |
| WO | WO 00/56228 | 9/2000 |
| WO | WO 00/60029 | 10/2000 |
| WO | WO 00/71032 | 11/2000 |
| WO | WO 01/21058 | 3/2001 |
| WO | WO 01/35832 | 5/2001 |
| WO | WO 01/47594 | 7/2001 |
| WO | WO 01/49186 | 7/2001 |
| WO | WO 01/91628 | 12/2001 |
| WO | WO 02/19915 | 3/2002 |
| WO | WO 02/19920 | 3/2002 |
| WO | WO 02/19922 | 3/2002 |
| WO | WO 02/19924 | 3/2002 |
| WO | WO 02/28286 | 4/2002 |
| WO | WO 02/38055 | 5/2002 |
| WO | WO 02/45593 | 6/2002 |
| WO | WO 02/45594 | 6/2002 |
| WO | WO 02/098302 | 12/2002 |
| WO | WO 03/013363 | 2/2003 |
| WO | WO 03/013364 | 2/2003 |
| WO | WO 03/047434 | 6/2003 |
| WO | WO 03/071955 | 9/2003 |
| WO | WO 03/071956 | 9/2003 |
| WO | WO 03/101310 | 12/2003 |
| WO | WO 03/071957 | 1/2004 |
| WO | WO 2004/004578 | 1/2004 |
| WO | WO 2004/060169 | 7/2004 |
| WO | WO 2004/069054 | 8/2004 |
| WO | WO 2005/082256 | 9/2005 |
| WO | WO 2005/115521 | 12/2005 |
| WO | WO 2006/000514 | 1/2006 |
| WO | WO 2006/083889 | 8/2006 |
| WO | PCT/US07/78051 | 9/2006 |
| WO | WO 2008/031102 | 9/2006 |
| WO | WO 2007/005585 | 1/2007 |
| WO | WO 2009/079091 | 6/2009 |
| ZA | 20010527 | 1/2001 |
| ZA | 200100528 | 1/2001 |

OTHER PUBLICATIONS

2006/0144479, Office Action, Oct. 16, 2007.
Stretch Comb by Scunci, retrieved via internet at www.scunci.com/productdetail by examiner on Oct. 9, 2007, publication date unavailable.
U.S. Appl. No. 09/866,551, filed May 25, 2001.
U.S. Appl. No. 11/396,141, filed Mar. 31, 2006.
U.S. Appl. No. 11/675,462, filed Feb. 15, 2007.
U.S. Appl. No. 11/744,089, filed May 3, 2007.
2002/0072768, Office Action, Aug. 27, 2004.
2002/0072768, Office Action, Feb. 23, 2005.
2002/0072768, Office Action, Apr. 11, 2005.
2002/0072768, Office Action, Jul. 27, 2005.
2002/0072768, Office Action, Mar. 6, 2006.
2002/0072768, Office Action, May 24, 2006.
2002/0072768, Office Action, Oct. 26, 2006.
2002/0072768, Office Action, Apr. 19, 2007.
2002/0133193, Office Action, Nov. 4, 2004.
2002/0133193, Office Action, May 4, 2005.
2002/0133193, Office Action, Oct. 18, 2005.
2002/0133193, Notice of Allowance, Apr. 18, 2007.
2002/0133193, Notice of Allowance, Sep. 27, 2007.
2003/0078598, Office Action, Feb. 9, 2005.
2003/0078598, Office Action, May 26, 2005.
2003/0078598, Office Action, Oct. 4, 2005.
2003/0078598, Notice of Allowance, May 10, 2006.
2003/0078598, Notice of Allowance, Jul. 2, 2007.
2003/0195561, Office Action, Jun. 10, 2004.
2003/0195561, Notice of Allowance, Sep. 21, 2004.
2003/0195561, Office Action, Jan. 3, 2006.
2003/0195561, Issue Notification, Feb. 15, 2006.

2003/0195561, Office Action, May 16, 2006.
2003/0195561, Notice of Allowance, Dec. 28, 2006.
2003/0195561, Notice of Allowance, Jul. 10, 2007.
2003/0195561, Notice of Allowance, Aug. 2, 2007.
2004/0153123, Office Action, Sep. 22, 2006.
2004/0153123, Office Action, Jan. 31, 2007.
2004/0153123, Office Action, Sep. 18, 2007.
2004/0153122, Office Action, Nov. 30, 2005.
2004/0153122, Office Action, Aug. 23, 2006.
2004/0153122, Office Action, Feb. 13, 2007.
2004/0153122, Office Action Sep. 12, 2007.
2004/0073255, Office Action, Sep. 15, 2006.
2004/0073255, Office Action, Apr. 18, 2007.
2004/0073236, Office Action, Sep. 19, 2006.
2004/0073236, Office Action, May 2, 2007.
2004/0009289, Office Action, Jun. 30, 2006.
2004/0009289, Office Action, Oct. 20, 2006.
2004/009289, Office Action, May 29, 2007.
2004/0167570, Office Action, Oct. 30, 2006.
2004/0167570, Office Action, Apr. 17, 2007.
2004/0167570, Office Action, Aug. 31, 2007.
2005/0274768, Office Action, Oct. 19, 2006.
2005/0274768, Office Action, Aug. 10, 2007.
2005/0216057, Office Action, Feb. 6, 2007.
2005/0216057, Office Action, May 30, 2007.
2005/0234508, Office Action, Aug. 13, 2007.
2006/0135989, Office Action, Nov. 30, 2006.
2006/0135989, Office Action, Sep. 5, 2007.
2006/0195124, Office Action, Jun. 6, 2007.
6,197,042, Notice of Allowance, Nov. 6, 2000.
6,197,042, Issue Notification, Feb. 15, 2001.
6,277,140, Office Action, Mar. 26, 2001.
6,277,140, Notice of Allowance, Jun. 4, 2001.
6,277,140, Issue Notification, Aug. 6, 2001.
6,391,048, Notice of Allowance, Mar. 26, 2001.
6,391,048, Office Action, Sep. 5, 2001.
6,391,048, Notice of Allowance, Feb. 11, 2002.
6,391,048, Issue Notification, May 3, 2002.
6,461,364, Notice of Allowance, May 6, 2002.
6,461,364, Issue Notification, Sep. 19, 2002.
6,582,452, Notice of Allowance, Jan. 31, 2003.
6,582,452, Issue Notification, Jun. 5, 2003.
6,616,686, Office Action, Dec. 17, 2002.
6,616,686, Notice of Allowance, Apr. 21, 2003.
6,616,686, Issue Notification, Aug. 21, 2003.
6,623,510, Notice of Allowance, Apr. 11, 2003.
6,623,510, Office Action, Jun. 9, 2003.
6,623,510, Issue Notification, Sep. 4, 2003.
6,632,238, Office Action, Feb. 26, 2003.
6,632,238, Notice of Allowance, Jun. 16, 2003.
6,632,238, Issue Notification, Sep. 25, 2003.
6,669,714, Office Action, Mar. 4, 2003.
6,669,714, Notice of Allowance, Jul. 28, 2003.
6,669,714, Issue Notification, Dec. 11, 2003.
6,695,867, Notice of Allowance, Sep. 29, 2003.
6,695,867, Issue Notification, Feb. 5, 2004.
6,719,777, Office Action, Feb. 20, 1987.
6,719,777 Notice of Allowance, Jul. 24, 1987.
6,719,777, Issue Notification, Mar. 25, 2004.
6,749,621, Notice of Allowance, Feb. 9, 2004.
6,749,621, Office Action, Apr. 13, 2004.
6,749,621, Issue Notification, May 27, 2004.
6,780,197, Office Action, Sep. 11, 2003.
6,780,197, Office Action, Feb. 9, 2004.
6,780,197, Notice of Allowance, Mar. 17, 2004.
6,780,197, Issue Notification, Aug. 5, 2004.
6,926,731, Office Action, Nov. 16, 2004.
6,926,731, Notice of Allowance, Apr. 6, 2005.
6,926,731, Issue Notification, Jul. 20, 2005.
6,942,674, Office Action, Sep. 29, 2004.
6,942,674, Notice of Allowance, May 13, 2005.
6,942,674, Issue Notification, Aug. 24, 2005.
7,001,398, Office Action, Mar. 22, 2005.

7,001,398, Notice of Allowance, Jul. 6, 2005.
7,001,398, Notice of Allowance, Oct. 5, 2005.
7,001,398, Issue Notification, Feb. 21, 2006.
7,008,435, Office Action, Apr. 20, 2005.
7,008,435, Office Action, Aug. 10, 2005.
7,008,435, Notice of Allowance, Oct. 18, 2005.
7,008,435, Issue Notification, Feb. 15, 2006.
7,108,709, Office Action, Jul. 27, 2004.
7,108,709, Office Action, Dec. 17, 2004.
7,108,709, Notice of Allowance, Mar. 9, 2005.
7,108,709, Office Action, Aug. 11, 2006.
7,108,709, Issue Notification, Aug. 30, 2006.
7,111,768, Office Action, Feb. 23, 2006.
7,111,768, Notice of Allowance, May 31, 2006.
7,111,768, Issue Notification, Sep. 6, 2006.
7,163,551, Office Action, Jan. 10, 2006.
7,163,551, Notice of Allowance, Sep. 20, 2006.
7,163,551, Issue Notification, Dec. 27, 2006.
7,211,101, Office Action, Aug. 10, 2005.
7,211,101, Office Action, Dec. 19, 2005.
7,211,101, Office Action, Apr. 21, 2006.
7,211,101, Notice of Allowance, Dec. 27, 2006.
7,211,101, Issue Notification, Apr. 11, 2007.
U.S. Appl. No. 11/852,190, dated Sep. 7, 2007, Carley.
U.S. Appl. No. 60/843,325, dated Sep. 8, 2006, Carley.
"Hand tool for forming telephone connections—comprises pliers with reciprocably driven ram crimping clip around conductors against anvil", Derwent-ACC-No. 1978-B8090A.
U.S. Appl. No. 60/843,325, filed Sep. 8, 2006, Carly.
U.S. Appl. No. 60/946,030, filed Jun. 25, 2007, Voss et al.
U.S. Appl. No. 60/946,042, filed Jun. 25, 2007, Ellingwood et al.
U.S. Appl. No. 12/106,928, filed Apr. 21, 2008, Ginn et al.
U.S. Appl. No. 12/106,937, filed Apr. 21, 2008, Ginn et al.
U.S. Appl. No. 12/113,092, filed Apr. 30, 2008, Ginn et al.
U.S. Appl. No. 12/113,851, filed May 1, 2008, Coleman et al.
U.S. Appl. No. 12/114,031, filed May 2, 2008, Coleman et al.
U.S. Appl. No. 12/114,091, filed May 2, 2008, Coleman et al.
U.S. Appl. No. 12/143,020, filed Jun. 20, 2008, Ellingwood et al.
U.S. Appl. No. 09/732,178, mailed Aug. 1, 2002, Office Action.
U.S. Appl. No. 09/732,178, mailed Dec. 24, 2002, Office Action.
U.S. Appl. No. 09/732,178, mailed Jun. 10, 2003, Advisory Action.
U.S. Appl. No. 09/732,178, mailed Jul. 3, 2003, Office Action.
U.S. Appl. No. 09/732,178, mailed Nov. 17, 2003, Notice of Allowance.
U.S. Appl. No. 10/006,400, mailed Apr. 2, 2008, Office Action.
U.S. Appl. No. 10/081,725, mailed Apr. 13, 2004, Office Action.
U.S. Appl. No. 10/147,774, mailed Feb. 4, 2008, Notice of Allowance.
U.S. Appl. No. 10/147,774, mailed Jun. 30, 2008, Office Action.
U.S. Appl. No. 10/264,306, mailed May 26, 2005, Office Action.
U.S. Appl. No. 10/264,306, mailed Feb. 4, 2008, Notice of Allowance.
U.S. Appl. No. 10/264,306, mailed Jun. 27, 2008, Office Action.
U.S. Appl. No. 10/356,214, mailed Mar. 6, 2008, Office Action.
U.S. Appl. No. 10/435,104, mailed May 23, 2007, Issue Notification.
U.S. Appl. No. 10/435,104, mailed Oct. 26, 2007, Notice of Allowance.
U.S. Appl. No. 10/435,104, mailed Apr. 4, 2008, Notice of Allowance.
U.S. Appl. No. 10/517,004, mailed Jan. 30, 2008, Office Action.
U.S. Appl. No. 10/541,083, mailed May 5, 2008, Office Action.
U.S. Appl. No. 10/616,832, mailed Jan. 22, 2008, Office Action.
U.S. Appl. No. 10/638,115, mailed Feb. 2, 2008, Office Action.
U.S. Appl. No. 10/667,144, mailed Nov. 19, 2007, Office Action.
U.S. Appl. No. 10/667,144, mailed Dec. 5, 2007, Office Action.
U.S. Appl. No. 10/667,144, mailed May 12, 2008, Office Action.
U.S. Appl. No. 10/682,459, mailed Apr. 2, 2008, Office Action.
U.S. Appl. No. 10/786,444, mailed Apr. 24, 2008, Office Action.
U.S. Appl. No. 10/787,073, mailed Feb. 22, 2008, Office Action.
U.S. Appl. No. 10/908,721, mailed Jan. 25, 2008, Office Action.
U.S. Appl. No. 11/113,549, mailed Nov. 9, 2007, Office Action.
U.S. Appl. No. 11/113,549, mailed Apr. 16, 2008, Office Action.
U.S. Appl. No. 11/152,562, mailed May 13, 2008, Office Action.

U.S. Appl. No. 11/344,891, mailed Apr. 29, 2008, Office Action.
U.S. Appl. No. 11/411,925, mailed Feb. 5, 2008, Office Action.
U.S. Appl. No. 60/696,069, filed Jul. 1, 2005, Pantages et al.
U.S. Appl. No. 60/946,026, filed Jun. 25, 2007, Ellingwood.
U.S. Appl. No. 10/435,104, mailed Dec. 22, 2008, Supplemental Notice of Allowability.
U.S. Appl. No. 10/541,083, mailed Dec. 29, 2008, Notice of Allowance.
U.S. Appl. No. 11/344,891, mailed Dec. 8, 2008, Office Action.
McCarthy, et al., "Tension (Stay) Suture Bridge", J. of International College of Surgeons, 34(5), pp. 613-614 (Nov. 1960).
U.S. Appl. No. 10/305,923, mailed Nov. 1, 2004, Office Action.
U.S. Appl. No. 10/305,923, mailed Mar. 3, 2005, Notice of Allowance.
U.S. Appl. No. 10/356,214, mailed Nov. 4, 2008, Office Action.
U.S. Appl. No. 10/435,104, mailed Nov. 14, 2007, Notice of Allowance.
U.S. Appl. No. 10/517,004, mailed Aug. 13, 2008, Notice of Allowance.
U.S. Appl. No. 10/541,083, mailed Oct. 31, 2007, Office Action.
U.S. Appl. No. 10/638,115, mailed Oct. 29, 2008, Office Action.
U.S. Appl. No. 10/682,459, mailed Dec. 4, 2008, Office Action.
U.S. Appl. No. 10/786,444, mailed Oct. 17, 2008, Office Action.
U.S. Appl. No. 10/787,073, mailed Nov. 12, 2008, Office Action.
U.S. Appl. No. 10/908,721, mailed Nov. 25, 2008, Office Action.
U.S. Appl. No. 11/461,323, mailed May 2, 2007, Office Action.
U.S. Appl. No. 11/461,323, mailed Oct. 29, 2007, Office Action.
U.S. Appl. No. 11/461,323, mailed Apr. 25, 2008, Office Action.
U.S. Appl. No. 11/461,323, mailed Nov. 6, 2008, Office Action.
U.S. Appl. No. 11/744,089, mailed Nov. 26, 2008, Office Action.
U.S. Appl. No. 12/393,877, filed Feb. 26, 2009, Ellingwood et al.
U.S. Appl. No. 12/402,398, filed Mar. 11, 2009, Carley et al.
U.S. Appl. No. 12/403,256, filed Mar. 12, 2009, Carley et al.
U.S. Appl. No. 12/403,277, filed Mar. 12, 2009, Coleman et al.
U.S. Appl. No. 09/680,837, mailed Jul. 9, 2002, Office Action.
U.S. Appl. No. 09/680,837, mailed Nov. 6, 2002, Office Action.
U.S. Appl. No. 09/680,837, mailed Mar. 25, 2003, Office Action.
U.S. Appl. No. 09/680,837, mailed Jun. 16, 2003, Notice of Allowance.
U.S. Appl. No. 09/680,837, mailed Sep. 11, 2003, Issue Notification.
U.S. Appl. No. 10/006,400, mailed Jan. 2, 2009, Office Action.
U.S. Appl. No. 10/147,774, mailed Mar. 18, 2009, Office Action.
U.S. Appl. No. 10/264, 306, mailed Feb. 26, 2009, Office Action.
U.S. Appl. No. 10/356,214, mailed Apr. 29, 2009, Office Action.
U.S. Appl. No. 10/517,004, mailed Feb. 10, 2009, Notice of Allowance.
U.S. Appl. No. 10/541,083, mailed Apr. 16, 2009, Notice of Allowance.
U.S. Appl. No. 10/638,115, mailed May 7, 2009, Notice of Allowance.
U.S. Appl. No. 10/667,144, mailed Mar. 24, 2009, Office Action.
U.S. Appl. No. 10/669,313, mailed Oct. 31, 2005, Office Action.
U.S. Appl. No. 10/669,313, mailed Jan. 11, 2006, Notice of Allowance.
U.S. Appl. No. 10/669,313, mailed Jun. 28, 2006, Notice of Allowance.
U.S. Appl. No. 10/669,313, mailed Nov. 15, 2006, Issue Notification.
U.S. Appl. No. 10/682,459, mailed Jun. 10, 2009, Office Action.
U.S. Appl. No. 11/048,503, mailed Mar. 13, 2009, Office Action.
U.S. Appl. No. 11/152,562, mailed Feb. 13, 2009, Office Action.
U.S. Appl. No. 11/344,793, mailed Jan. 22, 2009, Office Action.
U.S. Appl. No. 11/344,868, mailed Mar. 25, 2009, Office Action.
U.S. Appl. No. 11/344,891, mailed Feb. 26, 2009, Office Action.
U.S. Appl. No. 11/396,141, mailed May 22, 2009, Office Action.
U.S. Appl. No. 11/396,731, mailed Feb. 13, 2009, Office Action.
U.S. Appl. No. 11/396,731, mailed May 22, 2009, Office Action.
U.S. Appl. No. 11/411,925, mailed Jan. 12, 2009, Office Action.
U.S. Appl. No. 11/427,297, mailed Jan. 30, 2009, Office Action.
U.S. Appl. No. 11/532,325, mailed Feb. 23, 2009, Office Action.
U.S. Appl. No. 12/106,928, mailed Jan. 23, 2009, Office Action.
U.S. Appl. No. 12/106,937, mailed Mar. 30, 2009, Office Action.
U.S. Appl. No. 29/296,370, mailed Aug. 18, 2008, Office Action.
U.S. Appl. No. 29/296,370, mailed Dec. 2, 2008, Notice of Allowance.
U.S. Appl. No. 29/296,370, mailed Apr. 1, 2009, Notice of Allowance.
U.S. Appl. No. 10/006,400, mailed Jul. 9, 2009, Notice of Allowance.
U.S. Appl. No. 10/147,774, mailed Oct. 26, 2009, Office Action.
U.S. Appl. No. 10/264,306, mailed Aug. 13, 2009, Office Action.
U.S. Appl. No. 10/517,004, mailed Jun. 26, 2009, Notice of Allowance.
U.S. Appl. No. 10/541,083, mailed Sep. 30, 2009, Notice of Allowance.
U.S. Appl. No. 10/616,832, mailed Jul. 21, 2009, Office Action.
U.S. Appl. No. 10/667,144, mailed Nov. 23, 2009, Office Action.
U.S. Appl. No. 10/786,444, mailed Jun. 18, 2009, Office Action.
U.S. Appl. No. 10/787,073, mailed Aug. 13, 2009, Office Action.
U.S. Appl. No. 10/908,721, mailed Jun. 23, 2009, Office Action.
U.S. Appl. No. 11/048,503, mailed Jun. 26, 2009, Office Action.
U.S. Appl. No. 11/113,549, mailed Jul. 21, 2009, Office Action.
U.S. Appl. No. 11/152,562, mailed Jul. 6, 2009, Office Action.
U.S. Appl. No. 11/198,811, mailed Sep. 22, 2009, Office Action.
U.S. Appl. No. 11/344,891, mailed Oct. 7, 2009, Office Action.
U.S. Appl. No. 11/390,586, mailed Jun. 24, 2009, Office Action.
U.S. Appl. No. 11/396,141, mailed Aug. 26, 2009, Office Action.
U.S. Appl. No. 11/411,925, mailed Sep. 10, 2009, Office Action.
U.S. Appl. No. 11/427,297, mailed Sep. 15, 2009, Office Action.
U.S. Appl. No. 11/461,323, mailed Jul. 27, 2009, Office Action.
U.S. Appl. No. 11/532,325, mailed Jun. 17, 2009, Office Action.
U.S. Appl. No. 11/744,089, mailed Aug. 14, 2009, Office Action.
U.S. Appl. No. 11/958,295, mailed Aug. 27, 2009, Office Action.
U.S. Appl. No. 12/106,937, mailed Nov. 18, 2009, Office Action.
U.S. Appl. No. 12/106,928, mailed Oct. 5, 2009, Office Action.
U.S. Appl. No. 12/403,256, mailed Dec. 16, 2009, Restriction Requirement.
U.S. Appl. No. 60/693,531, filed Jun. 24, 2005, Carly.
Marshall A.C., Lock J.E., Structural and Compliant Anatomy of the Patent Foramen Ovale in Patients Undergoing Transcatheter Closure, Am Heart J Aug. 2000; 140(2); pp. 303-307.
Taber's Cyclopedic Medical Dictionary, 18th Ed. 1997, pp. 747 and 1420.
U.S. Appl. No. 10/006,400, mailed Jan. 13, 2010, Notice of Allowance.
U.S. Appl. No. 10/006,400, mailed Apr. 27, 2010, Notice of Allowance.
U.S. Appl. No. 10/264,306, mailed Jan. 27, 2010, Office Action.
U.S. Appl. No. 10/356,214, mailed Jan. 13, 2010, Notice of Allowance.
U.S. Appl. No. 10/435,104, mailed Jan. 20, 2010, Notice of Allowance.
U.S. Appl. No. 10/517,004, mailed Jan. 11, 2010, Notice of Allowance.
U.S. Appl. No. 10/517,004, mailed Apr. 23, 2010, Notice of Allowance.
U.S. Appl. No. 10/541,083, mailed Feb. 5, 2010, Notice of Allowance.
U.S. Appl. No. 10/616,832, mailed Jan. 11, 2010, Notice of Allowance.
U.S. Appl. No. 10/638,115, mailed Dec. 1, 2009, Notice of Allowance.
U.S. Appl. No. 10/638,115, mailed Apr. 2, 2010, Notice of Allowance.
U.S. Appl. No. 10/682,459, mailed Dec. 23, 2009, Office Action.
U.S. Appl. No. 10/682,459, mailed Apr. 28, 2010, Office Action.
U.S. Appl. No. 10/786,444, mailed Jan. 14, 2010, Office Action.
U.S. Appl. No. 10/787,073, mailed Feb. 17, 2010, Notice of Allowance.
U.S. Appl. No. 10/908,721, mailed Feb. 2, 2010, Office Action.
U.S. Appl. No. 11/048,503, mailed Jan. 11, 2010, Notice of Allowance.
U.S. Appl. No. 11/048,503, mailed Apr. 26, 2010, Notice of Allowance.
U.S. Appl. No. 11/152,562, mailed Mar. 31, 2010, Office Action.
U.S. Appl. No. 11/455,993, mailed Feb. 17, 2009, Office Action.
U.S. Appl. No. 11/455,993, mailed Dec. 16, 2009, Office Action.

U.S. Appl. No. 11/461,323, mailed Apr. 5, 2010, Notice of Allowance.
U.S. Appl. No. 11/532,325, mailed Jan. 5, 2010, Office Action.
U.S. Appl. No. 11/532,576, mailed Mar. 1, 2010, Office Action.
U.S. Appl. No. 11/532,576, mailed Apr. 23, 2010, Office Action.
U.S. Appl. No. 11/675,462, mailed Dec. 10, 2009, Office Action.
U.S. Appl. No. 11/767,818, mailed Dec. 24, 2009, Office Action.
U.S. Appl. No. 11/767,818, mailed Mar. 22, 2010, Office Action.
U.S. Appl. No. 11/959,334, mailed Aug. 19, 2009, Office Action.
U.S. Appl. No. 11/959,334, mailed Jan. 12, 2010, Notice of Allowance.
U.S. Appl. No. 11/959,334, mailed Apr. 14, 2010, Notice of Allowance.
U.S. Appl. No. 12/402,398, mailed Mar. 9, 2010, Office Action.
U.S. Appl. No. 12/403,256, mailed Mar. 30, 2010, Office Action.
U.S. Appl. No. 29/296,370, mailed Feb. 10, 2010, Issue Notification.
U.S. Appl. No. 61/139,995, filed Dec. 22, 2008, Clark.
U.S. Appl. No. 61/141,597, filed Dec. 30, 2008, Clark.
U.S. Appl. No. 12/481,377, filed Jun. 9, 2009, Clark.
U.S. Appl. No. 12/642,319, filed Dec. 18, 2009, Clark.
U.S. Appl. No. 60/793,444, filed Apr. 20, 2006, Jones et al.
U.S. Appl. No. 11/396,141, mailed May 4, 2010, Office Action.
U.S. Appl. No. 11/674,930, mailed Jan. 8, 2009, Office Action.
U.S. Appl. No. 11/674,930, mailed Jun. 4, 2009, Office Action.
U.S. Appl. No. 11/674,930, mailed Jan. 8, 2010, Office Action.
U.S. Appl. No. 10/356,214, mailed May 13, 2010, Notice of Allowance.
U.S. Appl. No. 10/541,083, May 10, 2010, Notice of Allowance.
U.S. Appl. No. 10/616,832, mailed May 12, 2010, Notice of Allowance.
U.S. Appl. No. 11/344,891, mailed May 7, 2010, Office Action.
U.S. Appl. No. 12/106,928, mailed May 10, 2010, Office Action.
U.S. Appl. No. 12/113,851, mailed Apr. 27, 2010, Office Action.
Deepak Mital et al, Renal Transplantation Without Sutures Using The Vascular Clipping System For Renal Artery And Vein Anastomosis - A New Technique, Transplantation Issue, Oct. 1996, pp. 1171-1173, vol. 62 - No. 8, Section of Transplantation Surgery, Department of General Surgery, Rush-Presbyterian/St. Luke's Medical Center, Chigago, IL.
DL Wessel et al, Outpatient closure of the patent ductus arteriosus, Circulation, May 1988, pp. 1068-1071, vol. 77 - No. 5, Department of Anesthesia, Children's Hospital, Boston, MA.
E Pikoulis et al, Arterial reconstruction with vascular clips is safe and quicker than sutured repair, Cardiovascular Surgery, Dec. 1998, pp. 573-578(6), vol. 6 - No. 6, Department of Surgery, Uniformed Services University of the Health Sciences, Bethesda, MD.
G Gershony et al, Novel vascular sealing device for closure of percutaneous vascular access sites, Cathet. Cardiovasc. Diagn., Jan. 1998, pp. 82-88, vol. 45.
H De Swart et al, A new hemostatic puncture closure device for the immediate sealing of arterial puncture sites, American journal of cardiology, Aug. 1993, pp. 445-449, vol. 72 - No. 5, Department of Cardiology, Academic Hospital Maastricht, The Netherlands.
Harrith M. Hasson M.D., Laparoscopic Cannula Cone with Means for Cannula Stabilization and Wound Closure, The Journal of the American Association of Gynecologic Laparoscopists, May 1998, pp. 183-185, vol. 5 - No. 2, Division of Obstetrics and Gynecology, University of Chicago, Chigago, IL.
J. Findlay et al, Carotid Arteriotomy Closure Using a Vascular Clip System, Neurosurgery, Mar. 1998, pp. 550-554, vol. 42 - No. 3, Division of Neurosurgery, University of Alberta, Edmonton, Canada.
Jeremy L Gilbert PhD, Wound Closure Biomaterials and Devices, Shock., Mar. 1999, p. 226, vol. 11- No. 3, Institution Northwestern University.
Jochen T. Cremer, MD, et al, Different approaches for minimally invasive closure of atrial septal defects, Ann. Thorac. Surg., Nov. 1998, pp. 1648-1652, vol. 67, a Division of Thoracic and Cardiovascular Surgery, Surgical Center, Hannover Medical School. Hannover, Germany.
K Narayanan et al, Simultaneous primary closure of four fasciotomy wounds in a single setting using the Sure-Closure device, Injury, Jul. 1996, pp. 449-451, vol. 27 - No. 6, Department of Surgery, Mercy Hospital of Pittsburgh, PA.

MD Gonze et al, Complications associated with percutaneous closure devices, Conference: Annual Meeting of the Society for Clinical Vascular Surgery, The American journal of surgery, Mar. 1999, pp. 209-211, vol. 178, No. 3, Department of Surgery, Section of Vascular Surgery, Ochsner Medical Institutions, New Orleans, LA.
MD Hellinger et al, Effective peritoneal and fascial closure of abdominal trocar sites utilizing the Endo-Judge, J Laparoendosc Surg., Oct. 1996, pp. 329-332, vol. 6 - No. 5, Orlando Regional Medical Center, FL.
Michael Gianturco, A Play on Catheterization, Forbes, Dec. 1996, p. 146, vol. 158 - No. 15.
Om Elashry et al, Comparative clinical study of port-closure techniques following laparoscopic surgery, Department of Surgery, Mallickrodt Institute of Radiography, J Am Coll Surg., Oct. 1996, pp. 335-344, vol. 183 - No. 4.
P M N Werker, et al, Review of facilitated approaches to vascular anastomosis surgery, Conference: Utrecht MICABG Workshop 2, The Annals of thoracic surgery, Apr. 1996, pp. S122-127, vol. 63 - No. 6, Department of Plastic, Reconstructive and Hand surgery, University Hospital Utrecht Netherlands Departments of Cardiology and Cardiopulmonary Surgery, Heart Lung Institute, Utrecht Netherlands.; Utrect University Hospital Utrecht Netherlands.
Peter Rhee MD et al, Use of Titanium Vascular Staples in Trauma, Journal of Trauma-Injury Infection & Critical Care, Dec. 1998, pp. 1097-1099, vol. 45 - No. 6, Institution from the Department of Surgery, Washington Hospital Center, Washington DC, and Uniformed Services University of the Health Sciences, Bethesda, Maryland.
ProstarXL - Percutaneous Vascular Surgical Device, www.Archive.org, Jun. 1998, Original Publisher: http://prostar.com, may also be found at http://web.archive.org/web/19980630040429/www.perclose.com/html/prstrxl.html.
SA Beyer-Enke et al, Immediate sealing of arterial puncture site following femoropopliteal angioplasty: A prospective randomized trial, Cardiovascular and Interventional Radiology 1996, Nov.-Dec. 1996, pp. 406-410, vol. 19 - No. 6, Gen Hosp North, Dept Dianost & Intervent Radiol, Nurnberg, Germany (Reprint).
Scott Hensley, Closing Wounds. New Devices seal arterial punctures in double time, Modern Healthcare (United States), Mar. 23, 2008, p. 48.
Sigmund Silber et al, A novel vascular device for closure of percutaneous arterial access sites, The American Journal of Cardiology, Apr. 1999, pp. 1248-1252, vol. 83 - No. 8.
Simonetta Blengino et al, A Randomized Study of the 8 French Hemostatic Puncture Closure Device vs Manual Compression After Coronary Interventions, Journal of the American College of Cardiology, Feb. 1995, p. 262A, vol. 25. - No. 2, Supplement 1.
Swee Lian Tan, MD, PhD, FACS, Explanation of Infected Hemostatic Puncture Closure Devices - A Case Report, Vascular and Endovascular Surgery, 1999, pp. 507-510, vol. 33 - No. 5, Parkland Medical Center, Derry, New Hampshire.
Sy Nakada et al, Comparison of newer laparoscopic port closure techniques in the porcine model, J Endourol, Oct. 1995, pp. 397-401, vol. 9 - No. 5, Department of Surgery/Urology, University of Wisconsin Medical School, Madison.
Thomas P. Baum RPA-C et al, Delayed Primary Closure Using Silastic Vessel Loops and Skin Staples: Description of the Technique and Case Reports, Annals of Plastic Surgery, Mar. 1999, pp. 337-340, vol. 42 - No. 3, Institution Department of Plastic and Reconstructive Surgery, Albert Einstein College of Medicine and Montefiore Medical Center, Bronx, NY.
Tomoaki Hinohara, Percutaneous vascular surgery (Prostar® Plus and Techstar® for femoral artery site closure), Interventional Cardiology Newsletter, May-Jul. 1997, pp. 19-28, vol. 5 - No. 3-4.
Ut Aker et al, Immediate arterial hemostasis after cardiac catheterization: initial experience with a new puncture closure device, Cathet Cardiovasc Diagn, Mar. 1994, pp. 228-232, vol. 33 - No. 3, Missouri Baptist Medical Center, St. Louis.
Wei Qu et al, An absorbable pinned-ring device for microvascular anastomosis of vein grafts: Experimental studies, Microsurgery 1999, Mar. 1999, pp. 128-134, vol. 19 - No. 3, Department of Orthopaedic Surgery, Hiroshima University School of Medicine, Hiroshima, Japan.

William G. Kussmaul III MD, et al., Rapid arterial hemostasis and decreased access site complications after cardiac catheterization and angioplasty: Results of a randomized trial of a novel hemostatic device, Journal of the American College of Cardiology, Jun. 1995, pp. 1685-1692, vol. 25 - No. 7.

U.S. Appl. No. 10/435,104, mailed Sep. 26, 2008, Notice Of Allowance.

U.S. Appl. No. 10/541,083, mailed Sep. 19, 2008, Notice Of Allowance.

U.S. Appl. No. 10/616,832, mailed Sep. 17, 2008, Office Action.

U.S. Appl. No. 10/198,811, mailed Aug. 26, 2008, Office Action.

* cited by examiner

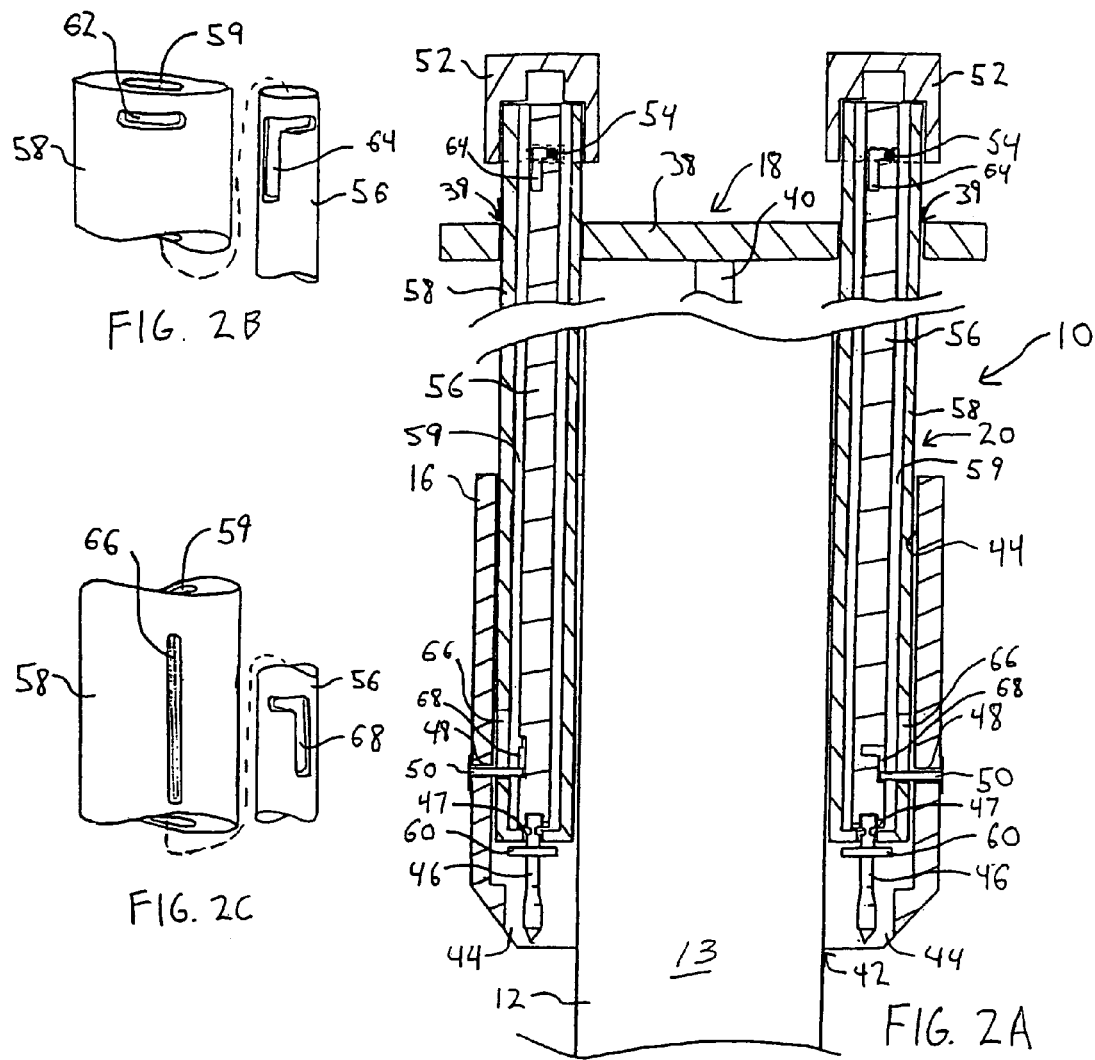

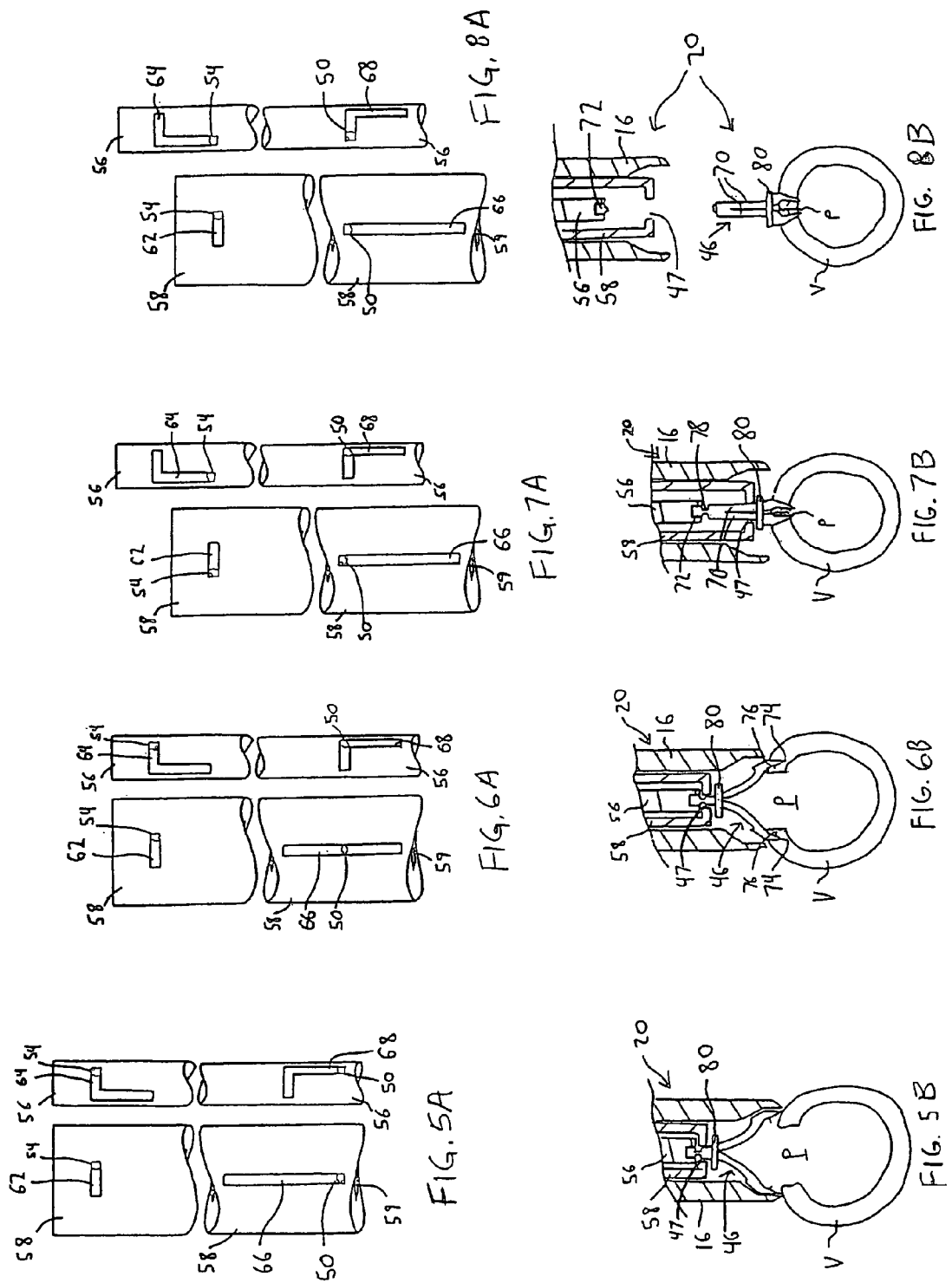

VASCULAR SHEATH WITH BIOABSORBABLE PUNCTURE SITE CLOSURE APPARATUS AND METHODS OF USE

CROSS-REFERENCE TO RELATED APPLICATIONS

This application is a continuation of U.S. patent application Ser. No. 10/264,306, filed Oct. 3, 2002, which is a continuation of U.S. patent application Ser. No. 09/546,998, filed Apr. 11, 2000 now U.S. Pat. No. 6,461,364 which is a continuation-in-part of U.S. patent application Ser. No. 09/478,179 filed Jan. 5, 2000, now U.S. Pat. No. 6,197,042, the disclosures of each are incorporated by reference herein.

BACKGROUND OF THE INVENTION

1. The Field of the Invention

The present invention relates to apparatus and methods for sealing an iatrogenic puncture in a vessel formed in conjunction with a diagnostic or therapeutic treatment. More particularly, the present invention provides apparatus comprising an introducer sheath including a puncture site closure device comprising a bioabsorbable clip.

2. The Relevant Technology

Catheterization and interventional procedures, such as angioplasty and stenting, generally are performed by inserting a hollow needle through a patient's skin and muscle tissue into the vascular system. A guide wire then is passed through the needle lumen into the patient's blood vessel. The needle is removed and an introducer sheath is advanced over the guide wire into the vessel. A catheter typically is passed through the lumen of the introducer sheath and advanced over the guide wire into position for a medical procedure. The introducer sheath therefore facilitates insertion of various devices into the vessel while minimizing trauma to the vessel wall and minimizing blood loss during a procedure.

Upon completion of the medical procedure, the catheter and introducer sheath are removed, leaving a puncture site in the vessel. Commonly, external pressure is applied until clotting and wound sealing occurs. However, this procedure is time consuming and expensive, requiring as much as an hour of a physician's or nurses' time, is uncomfortable for the patient, and requires that the patient be immobilized in the operating room, cathlab, or holding area. Furthermore, a risk of hematoma exists from bleeding prior to hemostasis.

Various apparatus have been developed for percutaneously sealing a vascular puncture by occluding or suturing the puncture site. For example, U.S. Pat. Nos. 5,192,302 and 5,222,974 to Kensey et al. describe the use of a biodegradable plug delivered through the introducer sheath into the puncture site. When deployed, the plug seals the vessel and provides hemostasis. Such devices have been slow to gain acceptance in the medical community, however, due to difficulties encountered in positioning the plug within the vessel.

Another previously known technique comprises percutaneously suturing the puncture site with specialized apparatus. Such apparatus is described, for example, in U.S. Pat. No. 5,304,184 to Hathaway et al. While percutaneous suturing devices may be effective, a significant degree of skill may be required on the part of the practitioner. Because such devices are mechanically complex, they tend to be relatively expensive to manufacture.

Surgical staples and resilient clips for external skin wound closure are well known in the art, Examples include U.S. Pat. No. 5,026,390 to Brown and U.S. Pat. No. 5,683,405 to Yacoubian et al, which both describe resiliently deformable closure devices suitable for manual external application.

To reduce the cost and complexity of percutaneous puncture closure devices, such devices employing resilient or deformable clips have been developed. U.S. Pat. No. 5,478,354 to Tovey et al. describes the use of resilient clips in conjunction with a trocar to close abdominal puncture wounds. U.S. Pat. No. 5,810,846 to Virnich et al. describes a specialized apparatus for closing a vascular puncture site with a plastically deformable clip. The apparatus preferably is advanced over a guide wire through a cannula to the surface of the puncture site, where the staple-like clips are delivered to close the wound.

U.S. Pat. No. 5,782,861 to Cragg et al. describes specialized apparatus for closing a puncture site with a detachable clip. The apparatus comprises a hollow shaft having a distal end formed with one or more opposed pairs of resilient grasping prongs and that is advanced over a guide wire through a coaxial hollow tube to a position at the distal end of the tube just proximal of the puncture. The grasping prongs are extended beyond the distal end of the tube to grasp the vessel on opposing sides of the puncture. The shaft then is partially retracted, causing the prongs to contract within the tube, thereby sealing the puncture site.

The percutaneous puncture closure devices described in the foregoing patents have the drawback that a separate device must be deployed through the introducer sheath to close the puncture site, thus prolonging the procedure. Moreover, these devices generally require relatively complex apparatus and involve time consuming manipulation to achieve hemostasis.

In view of the foregoing, it would be desirable to provide apparatus and methods suitable for vascular puncture closure that overcome the disadvantages of previously known devices.

It also would be desirable to provide apparatus and methods that quickly and effectively achieve hemostasis.

It further would be desirable to provide vascular puncture closure apparatus and methods that do not require the introduction of additional apparatus at the completion of the catheterization procedure to achieve closure.

It still further would be desirable to provide apparatus and methods wherein all foreign materials left in a patient's body are bioabsorbable.

It would be desirable to provide vascular puncture closure apparatus and methods that are safe, lower cost, and easy to use.

BRIEF SUMMARY OF THE INVENTION

In view of the foregoing, it is an object of the present invention to provide vascular puncture closure apparatus and methods that overcome disadvantages of previously known devices.

It also is an object of this invention to provide apparatus and methods suitable for vascular puncture closure that quickly and effectively achieve hemostasis.

It is a further object of the present invention to provide apparatus and methods for vascular puncture closure that do not require the introduction of additional apparatus at the completion of the catheterization procedure to achieve closure.

It is still further an object of the present invention to provide apparatus and methods wherein all foreign materials left in a patient's body are bioabsorbable.

It is yet another object of the present invention to provide vascular puncture closure apparatus and methods that are safe, lower cost, and easy to use.

These and other objects of the present invention are accomplished by providing a vascular introducer sheath having an integrated wound closure component. The closure component consists of a bioabsorbable and deformable clip with a bioabsorbable fastener and is disposed on and advanceable over the exterior of the introducer sheath in an expanded delivery configuration until opposite sides of the clip pierce a vessel on opposite sides of a puncture site. The clip is then mechanically deformed with the fastener into a deployed configuration, thereby drawing opposite sides of the puncture together and closing the wound. Means also are provided for confirming when the bioabsorbable clip has engaged the vessel wall to indicate to the surgeon that the clip may be deployed and the introducer sheath may be withdrawn.

In a preferred embodiment, the bioabsorbable clip resembles an inverted "Y" with pointed ends that puncture the vessel to be closed. The fastener comprises a bioabsorbable locking collar that may be advanced down the length of the clip to bring the pointed ends together.

In a second embodiment, the bioabsorbable clip comprises a hoop with pointed legs extending therefrom. The hoop has two points of reduced thickness spaced 180 degrees apart on the circumference of the hoop. The fastener comprises a bioabsorbable conical wedge that is pushed down into the hoop to force opposing sides of the hoop towards one another and bring the pointed legs together.

Advantageously, the wound closure component of the present invention is inexpensively integrated into a standard-size introducer sheath, thereby eliminating the need for a separate closure device at the conclusion of a catheterization procedure. The present invention provides quick, safe, effective, and easy-to-use apparatus for achieving vascular closure that overcome drawbacks of previously known devices. Methods of using the apparatus of the present invention also are provided.

BRIEF DESCRIPTION OF THE DRAWINGS

The above and other objects and advantages of the present invention will be apparent upon consideration of the following detailed description, taken in conjunction with the accompanying drawings, in which like reference characters refer to like parts throughout, and in which:

FIGS. 2A-2C are, respectively, a cross-sectional view of a closure component of the vascular device of FIG. 1, an exploded side view of proximal slots of the closure component, and an exploded side view of distal slots;

FIGS. 5A-5B through 8A-8B are side-sectional views of the closure component of FIG. 2A in use at a vascular puncture site, with corresponding side views of the proximal and distal slots of FIGS. 2B and 2C, illustrating a method of sealing the puncture site with the present invention.

DETAILED DESCRIPTION OF THE PREFERRED EMBODIMENTS

The integrated vascular introducer sheath with closure component of the present invention overcomes disadvantages associated with previously known methods and apparatus for sealing a vascular puncture by providing a quick, simple, safe, lower cost, effective, and easy-to-use solution to wound closure. Apparatus constructed in accordance with the present invention provide vascular introduction and wound closure in a single device, eliminating the time and manipulation required to insert a separate closure device at the completion of a procedure.

Figure 1:
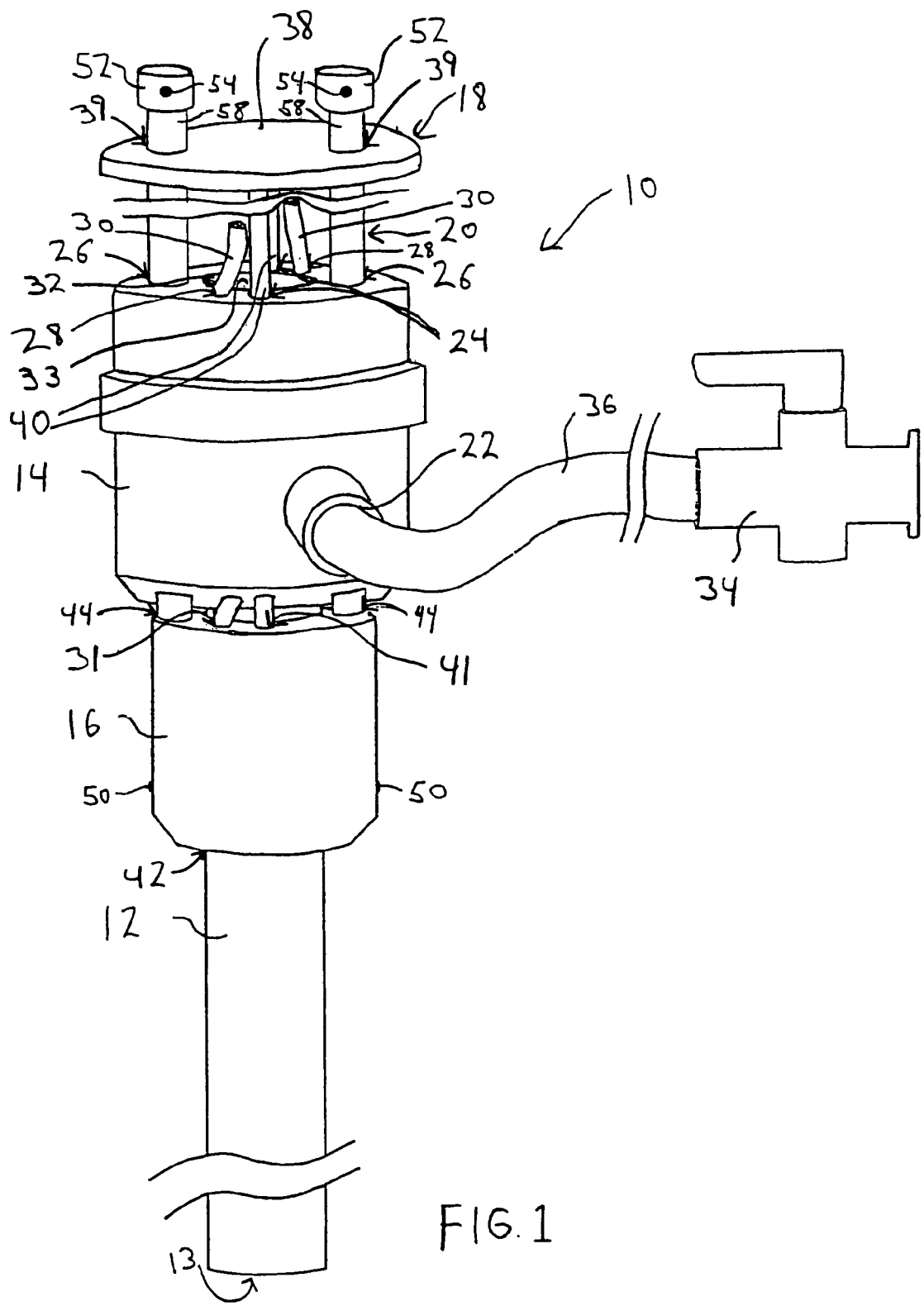
FIG. 1 is a side view of an integrated vascular device constructed in accordance with the present invention.

Referring to FIG. 1, a first embodiment of apparatus of the present invention is described. Vascular device 10 comprises introducer sheath 12 coupled to hub 14, clip housing 16 and clip actuator 18. A closure component 20, as described in detail hereinbelow, is disposed in clip housing 16.

Introducer sheath 12 comprises a material typically used for vascular introducer sheaths, such as polyethylene or nylon, and includes central lumen 13 through which other interventional devices may be introduced into the vasculature, for example, to perform a diagnostic or interventional procedure such as angiography, angioplasty, or stenting.

Hub 14 is mounted to the proximal end of introducer sheath 12 and includes side port 22, actuator lumens 24, closure lumens 26, backbleed lumens 28, backbleed tubes 30, and device port 32. Device port 32 communicates with central lumen 13 of introducer sheath 12, and has self-sealing elastomeric membrane 33 disposed across it. Self-sealing membrane 33, which may comprise, e.g., latex or a biocompatible synthetic rubber, permits interventional devices to be introduced through device port 32, while preventing blood loss through central lumen 13. Side port 22 of hub 14 is also in communication with central lumen 13, and is connected to hemostatic port 34 via biocompatible tubing 36.

Clip housing 16 includes two lumens, as described hereinbelow, that each holds a bioabsorbable, deformable clip. In accordance with the principles of the present invention, clip housing 16 is slidably disposed on the exterior of introducer sheath 12 and is movable from a stowed position, adjacent hub 14, to a distal clip deployment position, where the bioabsorbable clip is urged into engagement with tissue surrounding a vascular puncture. Clip housing 16 prevents the clips from snagging on tissue during advancement of clip housing 16.

Clip actuator 18 comprises plunger 38 and rods 40, which are configured to slidably pass through actuator lumens 24 of hub 14. Plunger 38 further includes openings 39. The distal ends of rods 40 are mounted in clip housing 16, so that movement of plunger 38 causes corresponding proximal or distal movement of clip housing 16. As described in detail hereinafter, when plunger 38 is moved to its proximal-most position, clip housing 16 is disposed adjacent to hub 14 and provides adequate clearance for interventional devices to be inserted through device port 32 and central lumen 13 into the patient's vasculature. When moved to its distal-most position, plunger 38 causes rods 40 to urge clip housing 16 distally.

Referring now also to FIGS. 2, closure component 20 of vascular device 10 is described in greater detail. Clip housing 16 comprises lumen 42 that slidably receives introducer sheath 12, rod bores 41 (see FIG. 1) in which rods 40 are mounted, clip lumens 44 in which bioabsorbable clips 46 are housed and advanced to a puncture site, pin holes 48 for rigidly receiving distal pins 50, and backbleed indicator ports (not shown, out of the plane of the cross-section of FIG. 2A) that are coupled to backbleed tubes 30 via blood lumens 31.

Closure component 20 further comprises caps 52 with pin holes (not shown, out of the plane of the cross-section of FIG. 2A) configured to receive proximal pins 54, clip holders 56 attached to bioabsorbable clips 46, and locking collar drivers 58 configured to advance fasteners 60. Locking collar drivers 58 are slidably received within lumens 39 of plunger 38, closure lumens 26 of hub 14, and clip lumens 44 of clip housing 16. Drivers 58 further comprise lumens 59 and square clip bores 47, in which clip holders 56 and clips 46, respectively, are slidably received. Bores 47 are of square cross section.

As illustrated in FIG. 2B, locking collar drivers 58 comprise proximal driver slots 62 that communicate with lumens 59, while clip holders 56 comprise proximal holder slots 64. Proximal pins 54, mounted in caps 52, pass through and are slidably received within slots 62 and 64. As seen in FIG. 2C, locking collar drivers 58 further comprise distal driver slots 66 that communicate with lumens 59, while clip holders 56 further comprise distal holder slots 68. Distal pins 50, mounted in clip housing 16, pass through and are slidably received within slots 66 and 68.

As discussed hereinabove, backbleed indicator ports (not shown) are coupled to backbleed tubes 30 via blood lumens 31 that extend through clip housing 16. Backbleed tubes 30 are slidably disposed through backbleed lumens 28 of hub 14. When the distal end of clip housing 16 is advanced distally against a vessel wall at a vascular puncture, blood enters the backbleed indicator ports and exits through tubes 30, providing visual confirmation to an operator that the distal end of clip housing 16 is positioned adjacent to the vessel wall. Backbleed tubes 30 thus enable the operator to determine when clip housing 16 has been sufficiently advanced to permit clip deployment, while reducing the risk that the clip is either deployed short of the puncture site or extended into the vessel.

In conjunction with clip deployment, a bioglue or tissue sealant may be delivered through hemostatic port 34, biocompatible tubing 36, side port 22 and central lumen 13 of introducer sheath 12 to the vascular puncture to further help seal the vessel after deployment of clips 46. Alternatively, the bioglue or tissue sealant may be delivered through device port 32 or through the backbleed path described above.

Figure 3A:
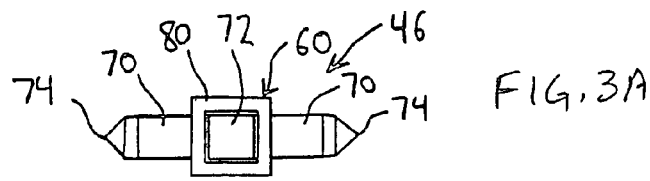
FIGS. 3A-3C are, respectively, views of a bioabsorbable clip and fastener of the present invention shown in top view in a delivery configuration, in side view in the delivery configuration, and in side view in a deployed configuration.
Figure 3C:
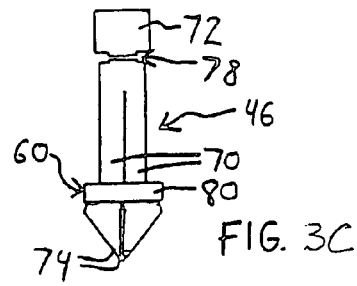
Figure 3B:
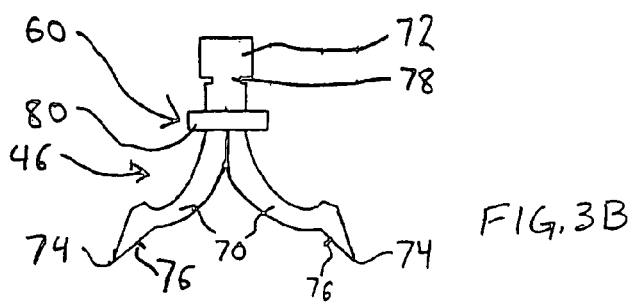

With reference now to FIGS. 3A-3C, bioabsorbable clip 46 and fastener 60 are described in greater detail. FIG. 3A shows clip 46 in the delivery configuration. Clip 46 comprises curved legs 70 and proximal end 72. Legs 70 distally terminate at spikes 74 with optional engagement means 76, and proximally terminate at narrowed region 78. Engagement means 76 may comprise, for example, barbs or hooks. As seen in FIG. 2A, proximal end 72 attaches to clip holder 56 by, for example, adhesive, and is slidably received by square clip bore 47 of locking collar driver 58. As with bore 47, clip 46 is of substantially square cross section.

Fastener 60 comprises bioabsorbable locking collar 80, which is slidably received on the exterior of clip 46. As seen in FIG. 3B, locking collar 80 may be distally advanced down the exterior of clip 46 to deform the clip to its deployed configuration, wherein curved legs 70 and spikes 74 are drawn together. Clip 46 may then be separated from clip holder 56 by rotating proximal end 72 with respect to legs 70, causing the clip to snap into two pieces at narrowed region 78, for the reasons described hereinafter. Clip 46 and locking collar 80 preferably are fabricated from bioabsorbable materials, such as polyglycolic acid.

Figure 4A:
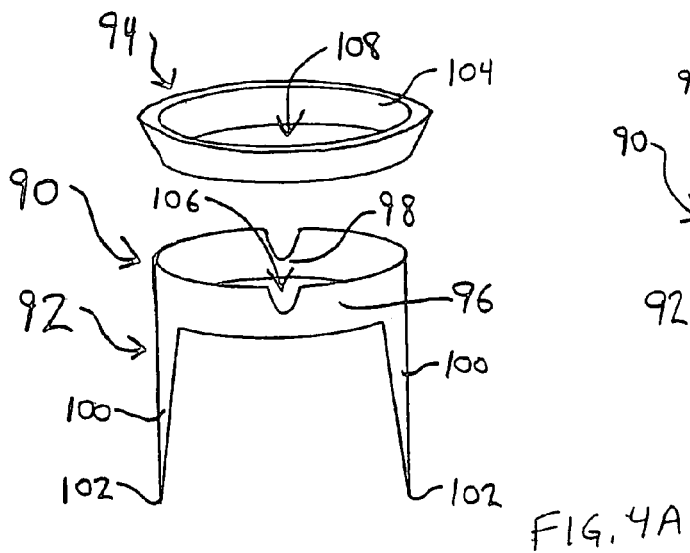
FIGS. 4A and 4B are isometric views of an alternative embodiment of the bioabsorbable surgical clip and fastener, constructed in accordance with the present invention and shown, respectively, in a delivery configuration and in a deployed configuration.
Figure 4B:
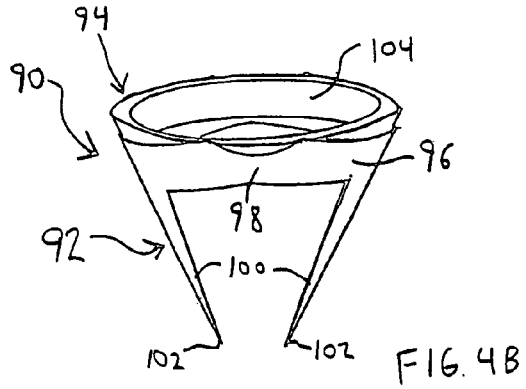

Referring to FIG. 4, an alternative embodiment of the closure component of the present invention is described. Closure component 90 comprises bioabsorbable clip 92 and fastener 94. Clip 92 comprises proximal hoop 96 with narrowed regions 98, and legs 100 terminating in spikes 102. Fastener 94 comprises bioabsorbable wedge 104. Wedge 104 has a diameter substantially equal to the diameter of hoop 96 at its distal end, the diameter tapering to a maximum diameter at the proximal end of wedge 104. Clip 92 therefore may be deformed from the delivery configuration of FIG. 4A to the deployed configuration of FIG. 4B, wherein legs 100 and spikes 102 are drawn together, by advancing wedge 104 into hoop 96 to deform clip 92 at narrowed regions 98. Lumen 106 extends through hoop 98 of clip 92, while lumen 108 extends through wedge 96. Clip 92 and wedge 96 therefore are configured for delivery over the exterior of an introducer sheath. The clip and wedge preferably are fabricated from bioabsorbable materials.

With reference to FIGS. 5A-5B through 8A-8B, in conjunction with FIGS. 1-3, methods of using vascular device 10 are described. Introducer sheath 12 is advanced through skin, fat, and muscle tissue into vessel V, through vascular puncture P, which is formed in accordance with well-known techniques. Vascular device 10 is used in the same manner as a standard introducer sheath, with instruments being advanced into the vessel via lumen 13. Specifically, with plunger 28 and rods 40 in the proximal-most, fully retracted position, an interventional procedure then is performed by introducing one or more interventional devices, e.g. angioplasty balloons, stent delivery systems, atherectomy devices, etc., through device port 32 and lumen 13 of introducer sheath 12 in accordance with well-known techniques. Side port 22 may be used to infuse fluids, e.g., contrast agents or medications, into the vessel through introducer sheath 12 during the interventional procedure.

Upon completion of the procedure, vascular device 10 advantageously may be used to close vascular puncture P. At this point, clip actuator 18, clip housing 16, and closure component 20 with clips 46, are disposed in the proximal-most position adjacent to hub 14.

Clip actuator 18 then is advanced by urging plunger 38 in the distal direction, thus causing rods 40 to slide through actuator lumens 24 of hub 14 and advance clip housing 16. Distal pins 50, mounted in housing 16, abut distal slots 66 and 68 of drivers 58 and holders 56, respectively. Thus, distal advancement of clip housing 16 also distally advances closure component 20. Continued distal advancement of plunger 38 causes the distal end of clip housing 16 to abut against the exterior of the vessel, so that the back bleed indicator ports (not shown) of clip housing 16 directly communicate with the puncture wound. The presence of pressure in the vessel higher than atmospheric pressure causes blood to pass through the indicator ports, through blood lumens 31, and exit through the proximal ends of tubes 30, thus confirming that clip housing 16 is positioned at the puncture site and should not be advanced further.

FIG. 5B illustrates closure component 20 via sectional views through clip housing 16 along planes parallel to introducer sheath 12. FIG. 5A shows the locations of proximal pins 54 within proximal slots 62 and 64, and the locations of distal pins 50 within distal slots 66 and 68, corresponding to the relative longitudinal positions of clip holders 56 and locking collar drivers 58 depicted in FIG. 5B. Pin locations are shown via side views of clip holders 56 and locking collar drivers 58 at the relevant locations.

As seen in FIGS. 5A and 5B, with clip housing 16 positioned at puncture site P, proximal pins 34, mounted in caps 52, are positioned at the extreme right of proximal driver slots 62 and of the circumferential portions of proximal holder slots 64. Distal pins 50 are located at the distal end of distal driver slots 66 and of the longitudinal portions of distal holder slots 68.

In FIGS. 6A and 6B, with clip housing 16 held inimobile, force is applied to caps 52 to distally advance clips 46 with respect to housing 16. Specifically, proximal pins 54 abut and apply force against proximal slots 62 and 64, which advances drivers 58 and clip holders 56, as well as attached clips 46 and locking collars 80. Distal pins 50 move freely within distal slots 66 and the longitudinal portions of distal slots 68. Distal advancement of clips 46 continues until pins 50 abut against the proximal end of the longitudinal portions of distal holder slots 68 of clip holders 56. Drivers 58 likewise are restrained by their connection to clip holders 56 via proximal pins 54. The tissue-engaging members, spikes 74 and engagement means 76, of clips 46 contact and pierce the wall of vessel V on opposite sides of the puncture site P.

As seen in FIGS. 7A and 7B, once the spikes have pierced the vessel wall, locking collar drivers 58 are advanced distally while clip housing 16 and clip holders 56 remain stationary, thereby distally advancing locking collars 80 down the exteriors of clips 46 to draw legs 70 and spikes 74 together to close puncture P. Engagement means 76 serve to retain the clips within the vessel wall during healing.

To achieve this advancement of drivers 58 with respect to clip holders 56, caps 52 are rotated clockwise, as viewed from above, until proximal pins 54 abut against the extreme left of proximal slots 62 and 64, thereby aligning the pins with the longitudinal portions of proximal holder slots 64. Then, force is once again applied to caps 52 to advance drivers 58 and deform clips 46 to their deployed configurations. Specifically, proximal pins 54 abut and apply force to proximal driver slots 62, thereby distally advancing drivers 58. Pins 54 move freely within the longitudinal portions of proximal holder slots 64 until they abut against the distal ends of slots 64. Likewise, distal driver slots 66 move freely until distal pins 50 abut the proximal ends of slots 66. In FIG. 7A, when proximal pins 54 abut slots 64 and distal pins 50 abut slots 66, locking collars 80 have been driven down the exteriors of clips 46, thereby deforming the clips to draw legs 70 together and close the puncture site.

In FIGS. 8A and 8B, with clips 46 deformed to seal puncture P, clip holders 56 are detached from clips 46 by snapping the clips free at narrowed regions 78. At this point, or prior to detachment, a suitable biocompatible bioglue or tissue sealant optionally may be injected into the puncture tract, as discussed hereinabove, through device port 32 or side port 22, to aid in sealing vascular puncture P. Alternatively, the bioglue or tissue sealant may be delivered through the backbleed path described above. Vascular device 10 then is withdrawn from the vessel wall, completing the procedure.

Clips 46 are detached from clip holders 56 by rotating caps 52 counterclockwise, as viewed from above. Proximal pins 54 of caps 52 move freely within proximal driver slots 62, but abut against the distal end of the longitudinal portions of proximal holder slots 64 and cause clip holders 56 to rotate with respect to collar drivers 58. Distal pins 50 of clip housing 16 move freely within the circumferential portions of distal holder slots 68 during rotation of clip holders 56. Meanwhile, drivers 58 are restrained from rotation by distal pins 50, which abut against distal driver slots 66. Bioabsorbable clips 46 do not rotate because the square cross section of square clip bores 47 of drivers 58 matches the substantially square cross section of clips 46; thus, since drivers 58 are restrained from rotation, so are clips 46. Non-square cross sections for clips 46 and bores 47, capable of performing the restraining function, will be apparent to those of skill in the art and fall within the scope of the present invention.

Since clips 46 are restrained while clip holders 56 rotate, and since proximal ends 72 of clips 46 are attached to clip holders 56, counterclockwise rotation of caps 52 causes clips 46 to snap at their weakest points: narrowed regions 78. Vascular device 10 may then be removed from the patient to complete the procedure.

Although preferred illustrative embodiments of the present invention are described above, it will be evident to one skilled in the art that various changes and modifications may be made without departing from the invention. For example, with minor modifications, vascular device 10 may be configured to carry closure component 90 of FIGS. 4, or any of a variety of alternative bioabsorbable and deformable clips. Proximal pins 54 may be formed integrally with caps 52, and distal pins 50 may be formed integrally with clip housing 16. Any number of clips 46 may be used to close the vascular puncture. It is intended in the appended claims to cover all such changes and modifications that fall within the true spirit and scope of the invention.

What is claimed is:

1. A closure component for sealing a puncture in a vessel wall comprising:
    a bioabsorbable clip, said clip having a delivery configuration, in which said clip has extending legs, and a deployed configuration, said legs of said clip comprising at least two elongated tissue-engaging members coupled to a proximal hoop, said proximal hoop having an inner surface; and
    a bioabsorbable fastener, said fastener having a wedging surface, said wedging surface of said fastener being configured to become wedged with said inner surface of said proximal hoop of said clip to move opposing legs of said clip to become directed inwardly towards one another to engage and close the puncture.

2. The closure component of claim 1, said wedging surface of said fastener having a wedge-like shape.

3. The closure component of claim 1, wherein said fastener has a circular configuration.

4. The closure component of claim 1, wherein said clip comprises a lumen, wherein said lumen includes said inner surface and receives said wedging surface of said fastener to cause said opposing legs of said clip to become directed inwardly towards one another.

5. The closure component of claim 1, wherein said proximal hoop comprises narrowed regions.

6. The closure component of claim 1, wherein each of said at least two elongated tissue-engaging members comprise a distally located spike.

7. The closure component of claim 1, wherein said bioabsorbable fastener is a unitary element.

8. The closure component of claim 7, wherein said bioabsorbable fastener has a proximal end and a distal end, said fastener having a distal diameter substantially equal to the diameter of said proximal hoop at said distal end of said fastener and a proximal diameter at said proximal end of said fastener, said proximal diameter being a maximum diameter of said fastener.

9. The closure component of claim 8, wherein said bioabsorbable fastener has an inner lumen.

10. A closure component for sealing a puncture in a vessel wall comprising:
    a bioabsorbable fastener having a wedging surface; and
    a bioabsorbable clip, said clip comprising at least two elongated tissue-engaging members coupled to a proximal hoop having a lumen with an inner surface configured to receive at least a portion of said wedging surface of said bioabsorbable fastener, said clip having a delivery configuration in which said at least two elongated tissue-engaging members extend longitudinally towards a proximal end of said clip and a deployed configuration in which said wedging surface of said fastener becomes wedged with said inner surface of said lumen of said clip to deform said clip to move opposing tissue-engaging members of said at least two elongated tissue-engaging members to become directed inwardly towards one another to engage and close the puncture.

11. The closure component of claim 10, wherein said fastener is shaped to deform said clip as said fastener moves from a proximal end toward a distal end of said clip.

12. The closure component of claim 11, wherein said fastener is shaped to cooperate with said lumen to deform said proximal hoop of said clip.

13. The closure component of claim 11, wherein said fastener comprises a tapered configuration.

14. The closure component of claim 10, wherein said proximal hoop comprises narrowed regions, said clip deforming at said narrowed regions.

15. The closure component of claim 10, wherein said bioabsorbable clip and said bioabsorbable fastener comprise a polyglycolic acid.

16. A method of sealing a puncture in a vessel wall, the method comprising:
    advancing a bioabsorbable clip having a proximal end and a distal end through the skin until said clip pierces the vessel wall on opposing sides of the puncture, said clip comprising longitudinally extending legs which comprise at least two elongated tissue-engaging members which are coupled to a proximal hoop; and
    wedging a bioadsorbable fastener with said clip to deform said clip with said bioabsorbable fastener by advancing said fastener from said proximal end of the clip toward said distal end of the clip and into said proximal hoop.

17. The method of claim 16, wherein said wedge has a circular configuration.

18. The method of claim 16, further comprising delivering a tissue sealant to the vessel wall in a vicinity of the puncture.

19. The method of claim 16, further comprising advancing a clip housing distally, said clip housing preventing said bioabsorbable clip from snagging on tissue during advancement through the tissue.

20. The method of claim 19, wherein advancing said bioabsorbable clip further comprises advancing a driver and a clip holder that retains said bioabsorbable clip toward the vessel wall.

* * * * *